United States Patent
Marubashi

(10) Patent No.: US 12,004,571 B2
(45) Date of Patent: Jun. 11, 2024

(54) INHALATION DEVICE WITH A CONTROLLER CAPABLE OF EXCHANGING AN ATOMIZER

(71) Applicant: Japan Tobacco Inc., Tokyo (JP)

(72) Inventor: Keiji Marubashi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 523 days.

(21) Appl. No.: 17/189,673

(22) Filed: Mar. 2, 2021

(65) Prior Publication Data

US 2021/0274848 A1 Sep. 9, 2021

(30) Foreign Application Priority Data

Mar. 5, 2020 (JP) ................... 2020-038094

(51) Int. Cl.
*A24F 40/53* (2020.01)
*A24F 40/10* (2020.01)
(Continued)

(52) U.S. Cl.
CPC .............. *A24F 40/53* (2020.01); *A24F 40/46* (2020.01); *A24F 40/57* (2020.01); *A61M 11/042* (2014.02);
(Continued)

(58) Field of Classification Search
CPC .......... A24F 40/10; A24F 40/20; A24F 40/30; A24F 40/46; A24F 40/50; A24F 40/53;
(Continued)

(56) References Cited

U.S. PATENT DOCUMENTS 6,795,715 B1 9/2004 Kubo et al.
10,045,567 B2 8/2018 Monsees et al.
(Continued)

FOREIGN PATENT DOCUMENTS

JP 11-215716 A 8/1999
JP 2000-278659 A 10/2000
(Continued)

OTHER PUBLICATIONS

Notice of Reasons for Refusal mailed on Jun. 15, 2020, received for JP Application 2020-038094, 13 pages including English Translation.

(Continued)

*Primary Examiner* — Abdullah A Riyami
*Assistant Examiner* — Thang H Nguyen
(74) *Attorney, Agent, or Firm* — XSENSUS LLP

(57) ABSTRACT

An inhalation device controller includes a holding portion configured to hold an atomizer including a heater configured to heat an aerosol source, a power supply unit configured to supply power to the heater of the atomizer attached to the holding portion, an amplifier to which a voltage according to a voltage of a node on a current path configured to supply the power to the heater is input, and a processor configured to acquire information from the amplifier and execute control according to the information. A first range that a value of the information takes in a holding state in which the holding portion holds the atomizer and a second range that the value of the information takes in a non-holding state in which the holding portion does not hold the atomizer do not include ranges overlapping each other.

15 Claims, 32 Drawing Sheets

(51) Int. Cl.

| | |
|---|---|
| *A24F 40/20* | (2020.01) |
| *A24F 40/46* | (2020.01) |
| *A24F 40/57* | (2020.01) |
| *A61M 11/04* | (2006.01) |
| *A61M 15/06* | (2006.01) |
| *G05B 1/01* | (2006.01) |
| *H05B 3/00* | (2006.01) |
| *A24F 40/30* | (2020.01) |
| *H02J 7/00* | (2006.01) |

(52) U.S. Cl.
CPC .............. *A61M 15/06* (2013.01); *G05B 1/01* (2013.01); *H05B 3/0014* (2013.01); *A24F 40/10* (2020.01); *A24F 40/20* (2020.01); *A24F 40/30* (2020.01); *A61M 2205/52* (2013.01); *A61M 2205/8206* (2013.01); *H02J 7/0063* (2013.01)

(58) Field of Classification Search
CPC . A24F 40/57; A61M 11/042; A61M 15/0021; A61M 15/0063; A61M 15/06; A61M 2205/121; A61M 2205/123; A61M 2205/127; A61M 2205/3331; A61M 2205/3368; A61M 2205/3653; A61M 2205/505; A61M 2205/52; A61M 2205/8206; G05B 1/01; H02J 7/0063; H05B 3/0014
See application file for complete search history.

(56) References Cited

U.S. PATENT DOCUMENTS

| | | | |
|---|---|---|---|
| 10,058,124 B2 | 8/2018 | Monsees et al. | |
| 10,264,823 B2 | 4/2019 | Monsees et al. | |
| 10,306,923 B2* | 6/2019 | Kananen | A24F 40/50 |
| 10,701,975 B2 | 7/2020 | Bowen et al. | |
| 2015/0208729 A1 | 7/2015 | Monsees et al. | |
| 2017/0112191 A1* | 4/2017 | Sur | A24F 40/50 |
| 2018/0020735 A1* | 1/2018 | Bilat | H05B 1/0277 |
| 2018/0064174 A1 | 3/2018 | Monsees et al. | |
| 2018/0070643 A1 | 3/2018 | Monsees et al. | |
| 2018/0070647 A1 | 3/2018 | Monsees et al. | |
| 2018/0077967 A1 | 3/2018 | Hatton et al. | |
| 2018/0092405 A1 | 4/2018 | Monsees et al. | |
| 2018/0092406 A1 | 4/2018 | Monsees et al. | |
| 2019/0158938 A1* | 5/2019 | Bowen | A61M 11/042 |
| 2019/0274353 A1* | 9/2019 | Sur | A61M 15/06 |
| 2019/0364971 A1* | 12/2019 | Soriano | A61M 11/042 |
| 2020/0037668 A1* | 2/2020 | Robert | A24B 15/167 |
| 2020/0352248 A1 | 11/2020 | Yamada et al. | |
| 2020/0375259 A1 | 12/2020 | Mizuguchi et al. | |

FOREIGN PATENT DOCUMENTS

| | | | |
|---|---|---|---|
| JP | 2005-114401 A | 4/2005 | |
| JP | 2012-200052 A | 10/2012 | |
| JP | 2013-35724 A | 2/2013 | |
| JP | 2013-97875 A | 5/2013 | |
| JP | 2016-531549 A | 10/2016 | |
| JP | 2017501805 A | 1/2017 | |
| JP | 6613008 B1 | 11/2019 | |
| WO | 2017/144374 A1 | 8/2017 | |
| WO | 2018/166925 A1 | 9/2018 | |
| WO | 2019/141577 A1 | 7/2019 | |
| WO | 2019/146062 A1 | 8/2019 | |
| WO | WO-2019146062 A1 * | 8/2019 | .............. A24D 1/20 |
| WO | 2020/006305 A1 | 1/2020 | |

OTHER PUBLICATIONS

Decision of Refusal mailed on Oct. 19, 2020, received for JP Application 2020-038094, 5 pages including English Translation.
Notice of Reasons for Refusal mailed on Jun. 8, 2020, received for JP Application 2020-038093, 9 pages including English Translation.
Decision to Grant mailed on Jul. 20, 2020, received for JP Application 2020-038093, 8 pages including English Translation.
Partial European search report issued on Aug. 2, 2021, in corresponding European patent Application No. 21159888.3, 17 pages.
Extended European search report issued on Jul. 27, 2021, in corresponding European patent Application No. 21159900.6, 8 pages.
Office Action issued on Jul. 16, 2021, in corresponding U.S. Appl. No. 17/189,867, 9 pages.

\* cited by examiner

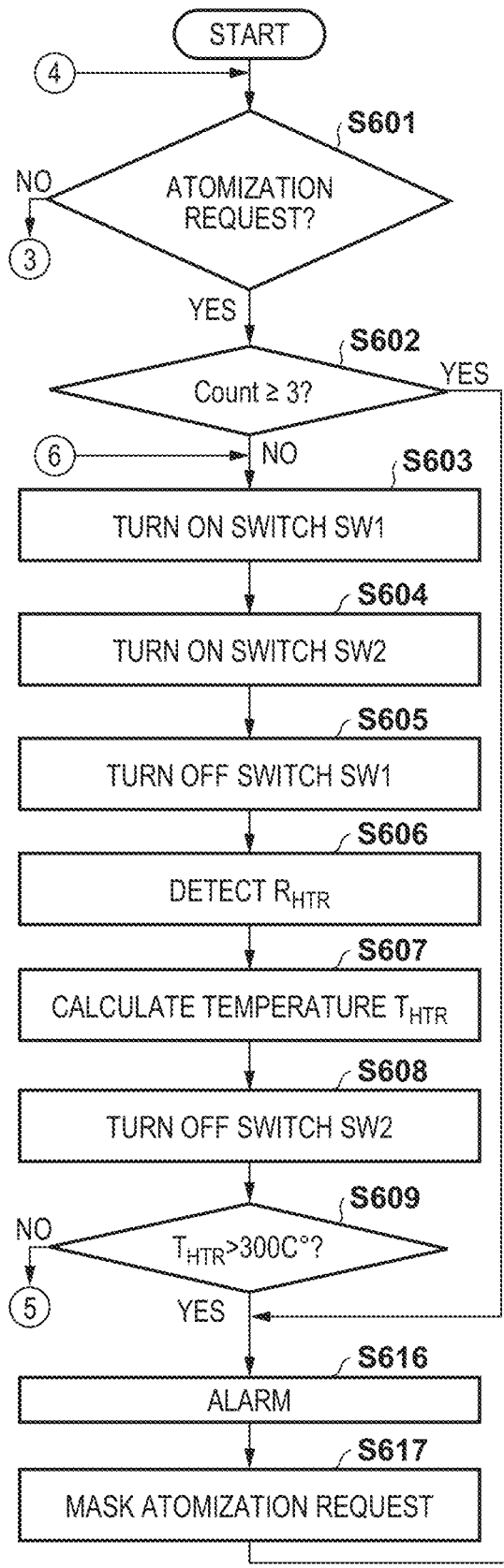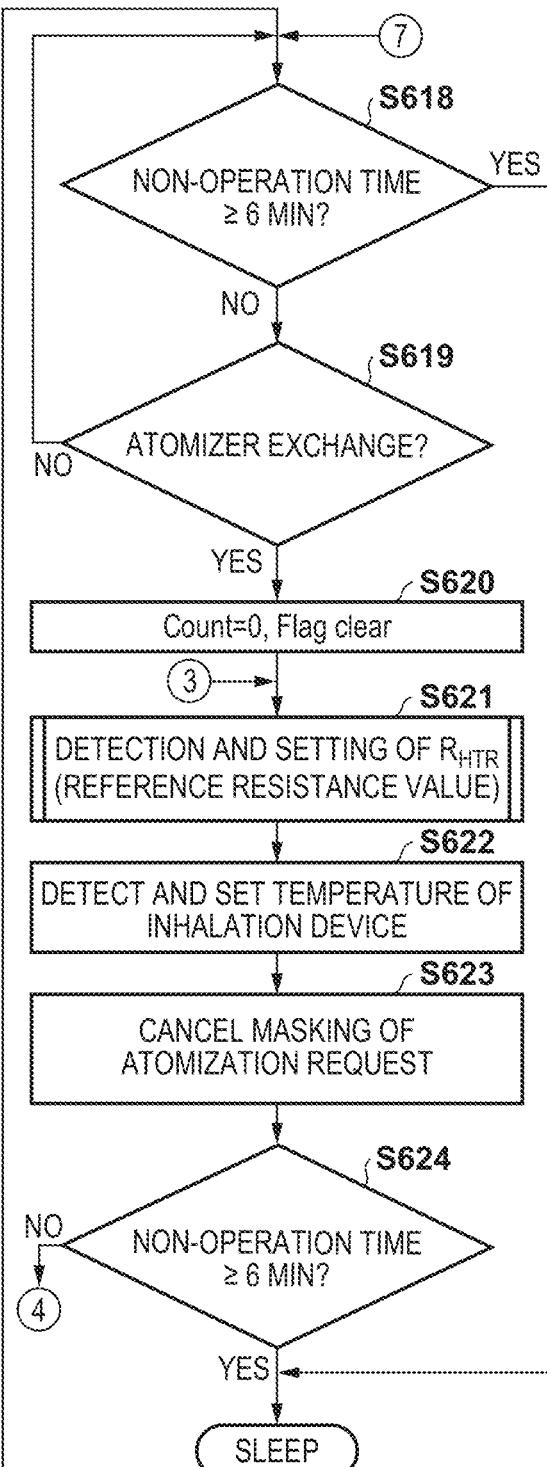
FIG. 6A

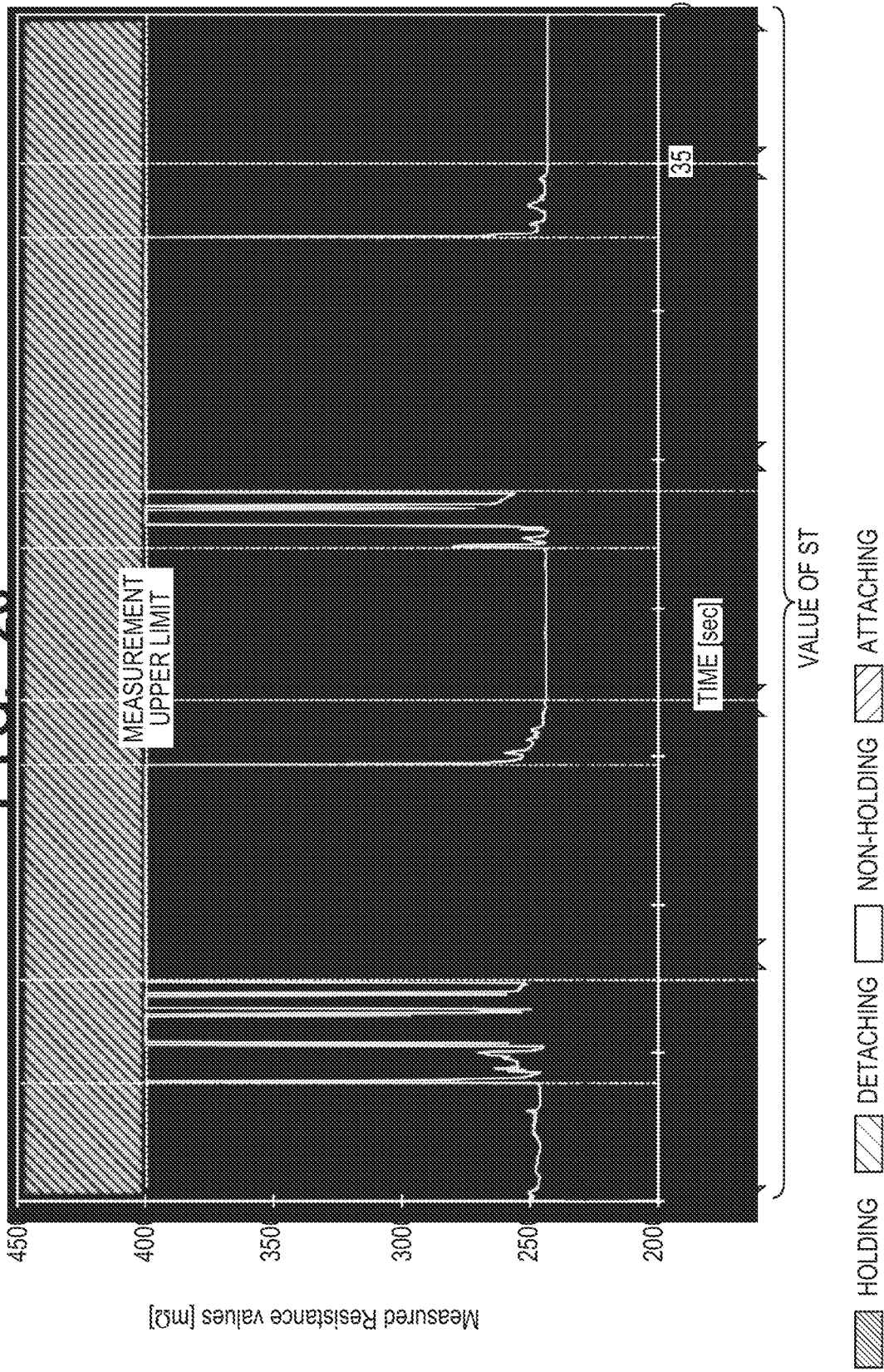

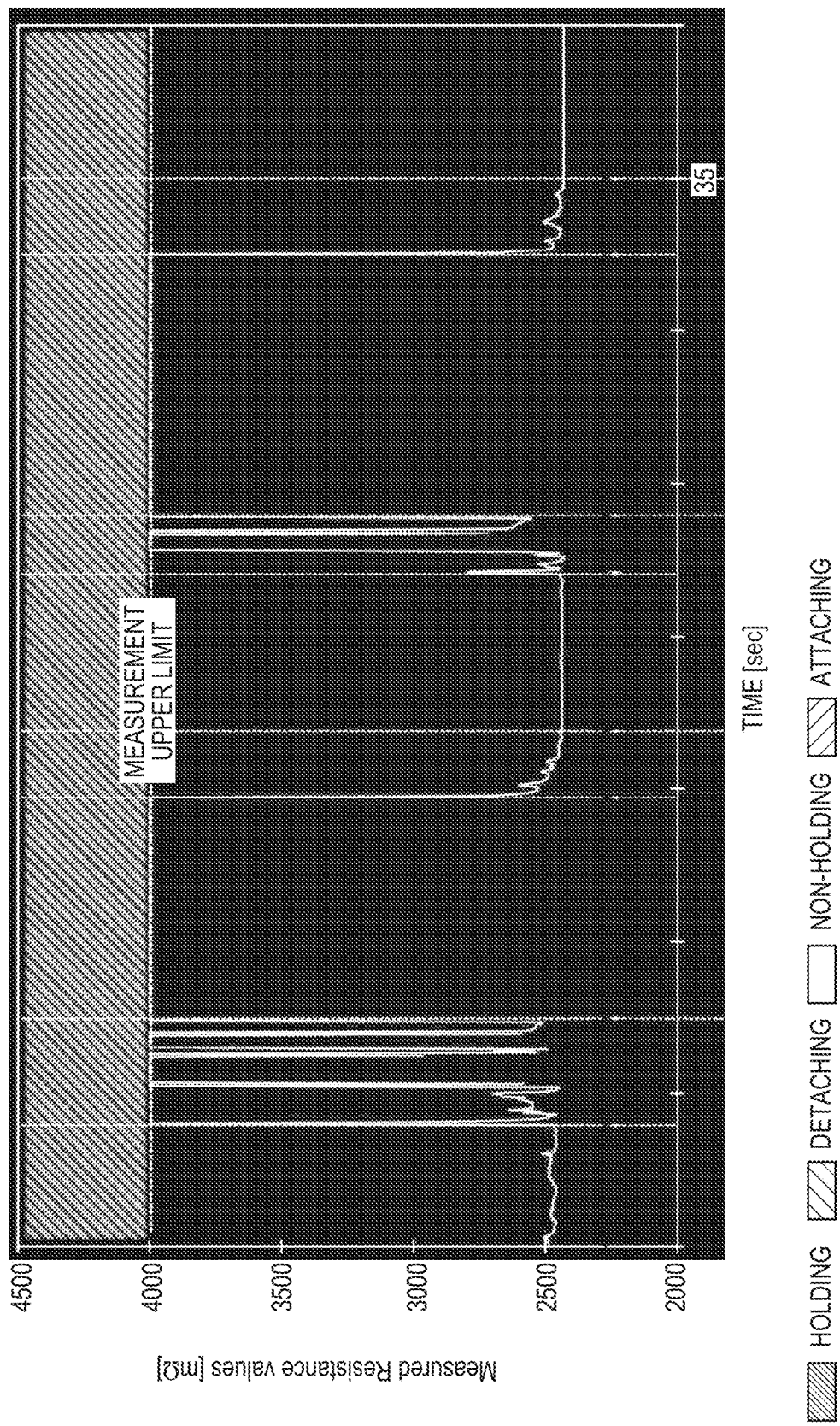

INHALATION DEVICE WITH A CONTROLLER CAPABLE OF EXCHANGING AN ATOMIZER

CROSS-REFERENCE TO RELATED APPLICATIONS

The present invention contains subject matter related to Japanese Patent Application No. 2020-038094 filed in the Japan Patent Office on Mar. 5, 2020, the entire contents of which are incorporated herein by reference. This application is also related to U.S. patent application Ser. No. 17/189,867, entitled "INHALATION DEVICE CONTROLLER", filed on the same day as this application and hereby incorporated by reference.

BACKGROUND OF THE INVENTION

Field of the Invention

The present invention relates to an inhalation device controller.

Description of the Related Art

Japanese Patent Application Laid-Open No. 2016-531549 describes a vaporizer having a battery compartment and a liquid compartment. The liquid compartment includes a heating element and the liquid to be heated. The liquid compartment is removable from the battery compartment. Upon receiving an input from a user, the vaporizer measures the resistance of the heating element and measures the voltage corresponding to that resistance.

In a suction device in which an atomizer having a heater that heats the aerosol source is replaceable, it is advantageous in reducing the cost of the device to communize a circuit configuration for detecting the presence of the atomizer and a circuit configuration for acquiring information from the heater.

SUMMARY OF THE INVENTION

One aspect of the present invention provides a technique advantageous in reducing the cost of an inhalation device capable of exchanging an atomizer including a heater configured to heat an aerosol source.

One aspect of the present invention is related to an inhalation device controller, and the inhalation device controller comprises a holding portion configured to hold an atomizer including a heater configured to heat an aerosol source, a power supply unit configured to supply power to the heater of the atomizer attached to the holding portion, an amplifier to which a voltage according to a voltage of a node on a current path configured to supply the power to the heater is input, and a processor configured to acquire information from the amplifier and execute control according to the information, wherein a first range that a value of the information can take in a holding state in which the holding portion holds the atomizer and a second range that the value of the information can take in a non-holding state in which the holding portion does not hold the atomizer do not include ranges overlapping each other.

In one embodiment, the processor can determine, based on the value of the information, whether a state of the holding portion is the holding state or the non-holding state.

In one embodiment, the processor can execute processing of acquiring the resistance value of the heater as a reference resistance value based on the value of the information in accordance with transition from the non-holding state to the holding state.

In one embodiment, the processor can calculate the temperature of the heater based on the value of the information and the reference resistance value.

In one embodiment, if the value of the information that was in the second range continuously falls within the first range, the processor can determine that the transition from the non-holding state to the holding state is completed.

In one embodiment, upon determining that the transition from the non-holding state to the holding state is completed, the processor can acquire and store the reference resistance value of the heater.

In one embodiment, in the holding state and in a state in which a request for operating the atomizer exists, the processor can control the power supply unit based on the reference resistance value and the resistance value of the heater, which is obtained based on the information, such that the heater obtains a target temperature.

In one embodiment, if the value of the information that was in the first range continuously falls within the second range, the processor can determine that the transition from the holding state to the non-holding state is completed.

In one embodiment, if the value of the information belongs to a third range in the first range in the holding state, the processor can control the power supply unit not to supply power to the heater.

In one embodiment, in the holding state and in a state in which a request for operating the atomizer exists, if the value of the information belongs to a fourth range in the first range, the processor can control the power supply unit based on the information, and the third range and the fourth range do not include ranges overlapping each other.

In one embodiment, the upper limit of the first range can be smaller than a power supply voltage supplied to the power supply terminal of the amplifier, and the lower limit of the second range can be larger than the upper limit of the first range.

In one embodiment, the second range can be a variation range of the power supply voltage.

In one embodiment, in the non-holding state, a voltage equal to the power supply voltage supplied to the power supply terminal of the amplifier can be input to the input terminal of the amplifier.

In one embodiment, the holding portion includes a first electrical contact and a second electrical contact, the first electrical contact is electrically connected to the output terminal of the power supply unit via a first resistive element and contacts a third electrical contact provided in the atomizer, the second electrical contact is electrically connected to a ground line and contacts a fourth electrical contact provided in the atomizer, and the amplifier can include a noninverting input terminal electrically connected to the first electrical contact, and an inverting input terminal electrically connected to the second electrical contact.

In one embodiment, the first electrical contact and the second electrical contact can electrically be connected by a second resistive element.

In one embodiment, letting $R_{shunt1}$ be the resistance value of the first resistive element, $R_{shunt2}$ be the resistance value of the second resistive element, $V_{out}$ be the voltage supplied to the first resistive element by the power supply unit, and $V_M$ be the power supply voltage supplied to the power supply terminal of the amplifier, $$(R_{shunt2}/(R_{shunt1}+R_{shunt2})) \cdot V_{out} > V_M$$

can be satisfied in the non-holding state.

In one embodiment, the inverting input terminal can be grounded via a third resistive element, and the inverting input terminal and the output terminal of the amplifier can be connected via a fourth resistive element.

Another aspect of the present invention is directed to an inhalation device controller, and the inhalation device controller comprises: a power supply unit configured to supply power to an atomizer including a heater configured to heat an aerosol source; a detection circuit configured to detect a resistance value of the heater; and a processor configured to generate a control signal in accordance with a smoothed signal generated by smoothing information obtained using the detection circuit.

In one embodiment, power supply to the atomizer by the power supply unit is stopped in accordance with the control signal.

In one embodiment, the processor can acquire, based on the smoothed signal, the resistance value of the heater at a given temperature as a reference resistance value of the heater.

In one embodiment, the processor can execute first processing of acquiring the reference resistance value and second processing of acquiring the temperature of the heater based on the information obtained using the detection circuit and the reference resistance value.

In one embodiment, the controller can further comprises a holding portion configured to hold the atomizer in a detachable state, wherein the processor executes the first processing in accordance with attachment of the atomizer to the holding portion.

In one embodiment, the processor can detect attachment of the atomizer to the holding portion based on a change of the resistance value, and executes the first processing in accordance with detection of the attachment.

In one embodiment, the processor can promote a user to do exchange via a user interface, and executes the first processing after waiting for an elapse of a predetermined time.

In one embodiment, the atomizer can include a capsule holder configured to hold a capsule including a flavor source in a detachable state, and In one embodiment, the holding portion can include a first electrical contact and a second electrical contact, the first electrical contact contacts a third electrical contact provided in the atomizer, the second electrical contact contacts a fourth electrical contact provided in the atomizer, the power supply unit can supply the power to the heater via the first electrical contact and the second electrical contact, and information obtained using the detection circuit can be affected by stress applied to the first electrical contact, the second electrical contact, the third electrical contact, and the fourth electrical contact when attaching the atomizer to the holding portion.

In one embodiment, the atomizer can include a capsule holder configured to hold a capsule including a flavor source in a detachable state, and the information obtained using the detection circuit can be affected by the stress applied to the first electrical contact, the second electrical contact, the third electrical contact, and the fourth electrical contact when attaching the capsule to the capsule holder.

In one embodiment, the processor can include a low pass filter configured to generate the smoothed signal by smoothing information sequentially obtained using the detection circuit. Alternatively, the processor can acquire the smoothed signal from a low pass filter configured to generate the smoothed signal by smoothing information sequentially obtained using the detection circuit.

In one embodiment, the processor can generate the smoothed signal by calculating an average value of information sequentially obtained using the detection circuit. Alternatively, the processor can acquire the smoothed signal generated by calculating an average value of information sequentially obtained using the detection circuit.

In one embodiment, the processor can calculate an average value of information sequentially obtained using the detection circuit, and can generate the smoothed signal based on information whose deviation amount from the average value is not more than a threshold in the information sequentially obtained using the detection circuit. Alternatively, the can processor acquire the smoothed signal generated based on information whose deviation amount from an average value of information sequentially obtained using the detection circuit is not more than a threshold in the information sequentially obtained using the detection circuit.

In one embodiment, the processor sequentially can calculate a differential value of information sequentially obtained using the detection circuit, and can generate the smoothed signal based on information whose differential value falls within a predetermined range in the information sequentially obtained using the detection circuit. Alternatively, the processor can acquire the smoothed signal generated based on information whose differential value of information sequentially obtained using the detection circuit falls within a predetermined range in the information sequentially obtained using the detection circuit.

In one embodiment, the processor can include an analog circuit configured to generate the smoothed signal from the information sequentially obtained using the detection circuit, and a microcontroller unit configured to generate the control signal in accordance with the smoothed signal from the analog circuit.

Still another aspect of the present invention is related to an inhalation device controller, and the inhalation device controller comprises a power supply unit configured to supply power to an atomizer including a heater configured to heat an aerosol source, a detection circuit configured to detect a resistance value of the heater, a smoothing circuit to which an output signal of the detection circuit is input, and a microcontroller unit to which an output signal of the smoothing circuit is input.

BRIEF DESCRIPTION OF THE DRAWINGS

FIGS. 6A and 6B show a flowchart showing detection associated processing of the inhalation device according to an embodiment;

FIG. 26 is a view showing transition of a control variable ST; and

FIG. 27 is a view showing a change of a state concerning holding and non-holding of the atomizer by the holding portion of a controller.

DESCRIPTION OF THE EMBODIMENTS

Figure 1:
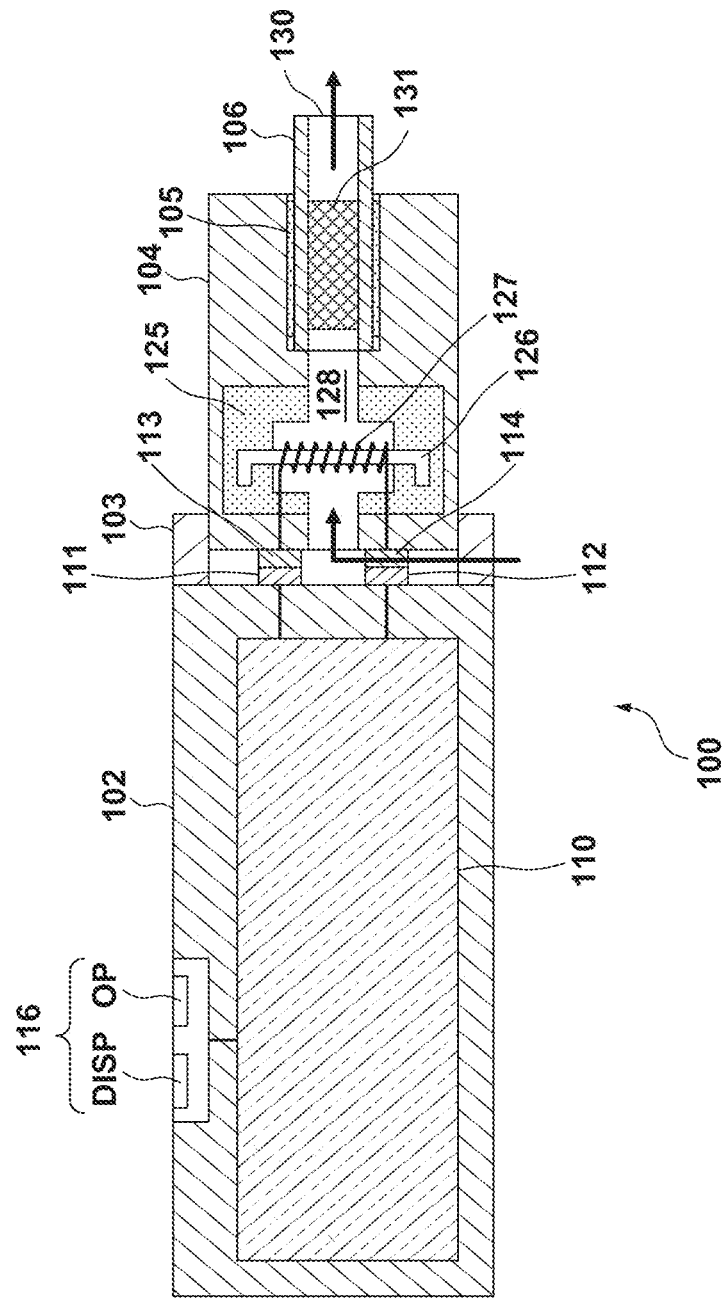
FIG. 1 is a view schematically showing the arrangement of an inhalation device according to an embodiment.

Hereinafter, embodiments will be described in detail with reference to the attached drawings. Note that the following embodiments are not intended to limit the scope of the claimed invention, and limitation is not made on an invention that requires all combinations of features described in the embodiments. Two or more of the multiple features described in the embodiments may be combined as appropriate. Furthermore, the same reference numerals are given to the same or similar configurations, and redundant description thereof is omitted.

FIG. 1 schematically shows the arrangement of an inhalation device 100 according to an embodiment. The inhalation device can be configured to provide a gas containing an aerosol or a gas containing an aerosol and a flavor substance to a user via a mouthpiece portion 130 in accordance with an inhalation operation of the user. The inhalation device 100 can include a controller 102 and an atomizer 104. The inhalation device 100 can include a holding portion 103 that holds the atomizer 104 in a detachable state. The controller 102 can be understood as an inhalation device controller. The atomizer 104 can be configured to atomize an aerosol source. The aerosol source can be, for example, a liquid such as a polyhydric alcohol such as glycerin or propylene glycerol. Alternatively, the aerosol source may contain a drug. The aerosol source may be a liquid, a solid, or a mixture of a liquid and a solid. A vapor source such as water may be used in place of the aerosol source.

The inhalation device 100 may further include a capsule 106 including a flavor source 131, and the atomizer 104 can include a capsule holder 105 that holds the capsule 106 in a detachable state. The capsule holder 105 may be included not in the atomizer 104 but in the controller 102. The flavor source 131 can be, for example, a molded body formed by molding a tobacco material. Alternatively, the flavor source 131 may be formed by a plant (for example, mint, herb, Chinese herb, coffee bean, and the like) other than tobacco. A flavor such as menthol may be added to the flavor source. The flavor source 131 may be added to the aerosol source.

The controller 102 can include an electric component 110. The electric component 110 can include a user interface 116. Alternatively, it may be understood that the controller 102 includes the electric component 110 and the user interface 116. The user interface 116 can include, for example, a display unit DISP (for example, a light emitting element such as an LED and/or an image display device such as an LCD) and/or an operation unit OP (for example, a switch such as a button switch and/or a touch display).

The holding portion 103 of the controller 102 can include a first electrical contact 111 and a second electrical contact 112. In a state in which the atomizer 104 is held by the holding portion 103, the first electrical contact 111 of the holding portion 103 can contact a third electrical contact 113 of the atomizer 104, and the second electrical contact 112 of the holding portion 103 can contact a fourth electrical contact 114 of the atomizer 104. The controller 102 can supply power to the atomizer 104 via the first electrical contact 111 and the second electrical contact 112. The first electrical contact 111 can electrically be connected to the ground line.

The atomizer 104 can include the third electrical contact 113 and the fourth electrical contact 114 described above. In addition, the atomizer 104 can include a heater 127 that heats the aerosol source, a container 125 that holds the aerosol source, and a transport portion (wick) 126 that transports the aerosol source held by the container 125 to a heating area by the heater 127. At least a part of the heating area can be arranged in a channel 128 provided in the atomizer 104. The first electrical contact 111, the third electrical contact 113, the heater 127, the fourth electrical contact 114, and the second electrical contact 112 form a current path configured to flow a current to the heater 127. The transport portion 126 can be made of, for example, a fiber material or a porous material.

As described above, the atomizer 104 can include the capsule holder 105 that detachably holds the capsule 106. In an example, the capsule holder 105 can hold the capsule 106 such that a part of the capsule 106 is stored in the capsule holder 105 or the atomizer 104, and the other part is exposed. The user can inhale a gas containing an aerosol by holding the mouthpiece portion 130 in the mouth. When the mouthpiece portion 130 is provided in the detachable capsule 106, the inhalation device 100 can be kept clean.

When the user holds the mouthpiece portion 130 in the mouth and performs an inhalation operation, air flows into the channel 128 of the atomizer 104 via an opening (not shown), and an aerosol generated by heating the aerosol source by the heater 127 is transported to the mouthpiece portion 130, as indicated by arrows. In the arrangement in which the flavor source 131 is arranged, a flavor substance generated from the flavor source 131 is added to the aerosol, transported to the mouthpiece portion 130, and inhaled into the mouth of the user.

Figure 2:
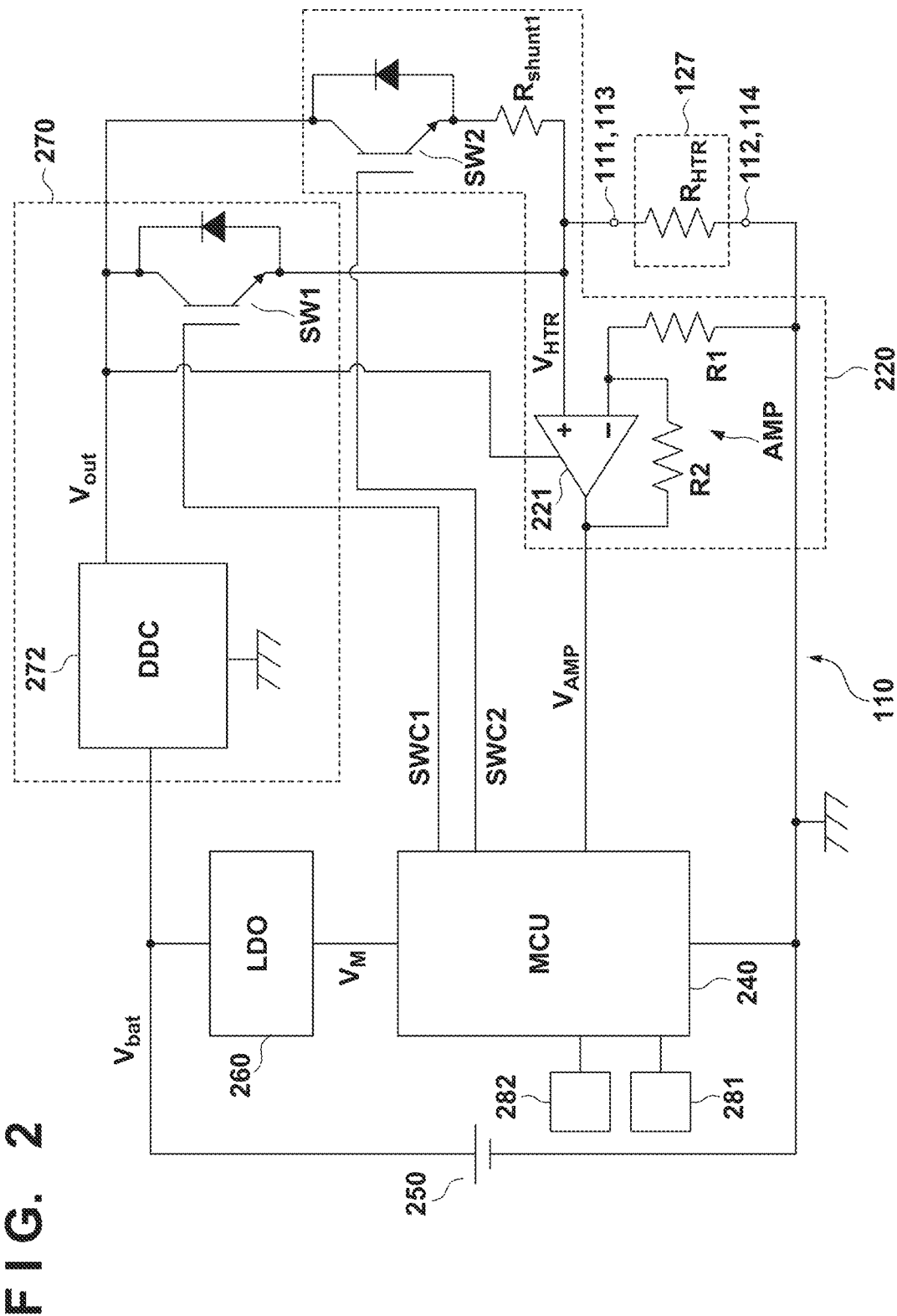
FIG. 2 is a view showing the first arrangement example of an electric component.

FIG. 2 shows the first arrangement example of the electric component 110. The electric component 110 can include a power supply (battery) 250, a power supply unit 270 that supplies power to (the heater 127 of) the atomizer 104, a detection circuit 220 configured to detect the resistance value of the heater 127, and a processor 240 that generates a control signal in accordance with information obtained using the detection circuit 220. The processor 240 can generate a control signal in accordance with, for example, a smoothed signal generated by smoothing information obtained using the detection circuit 220. The heater 127 has a resistance value $R_{HTR}$ that changes depending on the temperature of the heater 127.

The power supply unit 270 can include a switch SW1 arranged in a current path configured to supply a current to the heater 127. Opening/closing (off/on) of the switch SW1 can be controlled by a control signal SWC1 generated by the processor 240 in accordance with information (for example, a smoothed signal) obtained using the detection circuit 220. The power supply unit 270 can include, for example, a voltage converter 272 that converts a power supply voltage $V_{bat}$ supplied from the power supply 250 into a heater driving voltage $V_{out}$. The switch SW1 can be arranged to form a current path configured to supply a current to the heater 127 between the ground line and the supply line of the heater driving voltage $V_{out}$. The switch SW1 can be arranged, for example, between the heater 127 and the supply line of the heater driving voltage $V_{out}$. The detection circuit 220 can include a shunt resistor (first resistive element) $R_{shunt1}$ and a switch SW2, which are arranged, in series with the heater 127, between the ground line and the supply line of the heater driving voltage $V_{out}$. Also, the detection circuit 220 can include an amplifier AMP that detects a voltage $V_{HTR}$ applied to the heater 127. Here, the resistance value of the shunt resistor $R_{shunt1}$ will be expressed as $R_{shunt1}$, like the reference symbol. The amplifier AMP includes, for example, a differential amplifier 221 including a noninverting input terminal, an inverting input terminal, and an output terminal, a resistive element R1 that connects the inverting input terminal and the ground line, and a resistive element R2 that connects the inverting input terminal and the output terminal, and the voltage $V_{HTR}$ can be input to the noninverting input terminal. In this arrangement example, if the resistance value of the resistive element R1 is expressed as R1, and the resistance value of the resistive element R2 is expressed as R2, an amplification factor A of the amplifier AMP is (1+R2/R1). However, the arrangement and the amplification factor A of the amplifier AMP are not limited to this example, and another arrangement and another amplification factor may be employed. The switch SW2 can be controlled by a control signal SWC2 generated by the processor 240.

To detect the resistance value $R_{HTR}$ of the heater 127, the switch SW1 is turned off, and the switch SW2 is turned on. At this time, letting him be a current flowing to $R_{HTR}$, $R_{HTR}$ is given by $$R_{HTR} = V_{HTR}/I_{HTR} = V_{HTR} \cdot (R_{HTR} + R_{shunt1})/V_{out} \quad (1)$$

When equation (1) is deformed, we obtain equation (2) that gives $R_{HTR}$.

$$R_{HTR} = R_{shunt1} \cdot V_{HTR}/(V_{out} - V_{HTR}) \quad (2)$$

An output voltage $V_{AMP}$ of the amplifier AMP of the detection circuit 220 is given by $$V_{AMP} = A \cdot V_{HTR} \quad (3)$$

When equation (3) is deformed, we obtain equation (4) that gives $V_{HTR}$.

$$V_{HTR} = V_{AMP}/A \quad (4)$$

Hence, the resistance value $R_{HTR}$ of the heater 127 can be obtained in accordance with equations (2) and (4).

The processor 240 can include an input terminal to which the output voltage $V_{AMP}$ of the amplifier AMP of the detection circuit 220 is input, and an A/D converter that converts an analog signal that is a voltage input to the input terminal into a digital signal. The processor 240 can generate a control signal in accordance with information (here, $V_{AMP}$) obtained using the detection circuit 220, for example, a smoothed signal obtained by smoothing the information. The control signal can be, for example, the control signal SWC1 but can include another control signal (for example, a control signal that controls the display unit DISP).

The processor 240 can be formed by, for example, an MCU (Micro Controller Unit). However, the processor 240 may be formed by an MCU and an analog circuit. To the processor 240, a voltage $V_M$ can be supplied from a voltage conversion circuit 260 such as an LDO (Low DropOut) that converts the power supply voltage $V_{bat}$ into the power supply voltage $V_M$ for the processor 240. The processor 240 can calculate the resistance value $R_{HTR}$ of the heater 127 in accordance with equations (2) and (4) based on $R_{shunt1}$ that is a known value, $V_{out}$, and $V_{AMP}$ that is supplied from the amplifier AMP.

The processor 240 can calculate the temperature of the heater 127 in accordance with equation (5) based on the resistance value $R_{HTR}$ of the heater 127.

$$T = T_{ref} + (1/\alpha) \cdot (R_{HTR} - R_{ref}) \cdot (1/R_{ref}) \cdot 10^6 \quad (5)$$

where $T_{ref}$ is a reference temperature. $R_{ref}$ is a reference resistance value, and this is the resistance value $R_{HTR}$ of the heater 127 at the reference temperature. α is the temperature coefficient [ppm/° C.] of the heater 127. Note that the reference temperature can be an arbitrary temperature, and the temperature of the heater 127 when acquiring the reference resistance value is the reference temperature. As the temperature of the heater 127 when acquiring the reference resistance value, the temperature of an arbitrary portion in the inhalation device 100 (for example, a temperature detected by a temperature sensor 282 to be described later) can be used as a substitute.

Based on the temperature of the heater 127, the processor 240 can generate the control signal SWC1 used to control the switch SW1 such that the temperature of the heater 127 matches a target temperature. The processor 240 receives a signal from the operation unit OP of the user interface 116, and provides a signal for display control to the display unit DISP of the user interface 116. The electric component 110 can include a puff sensor (for example, a pressure sensor) 281 that detects the puff operation of the user, and the temperature sensor 282 that detects the temperature of a predetermined portion of the electric component 110. The temperature sensor 282 may be incorporated in the puff sensor 281, the power supply 250, or the processor 240.

Figure 3:
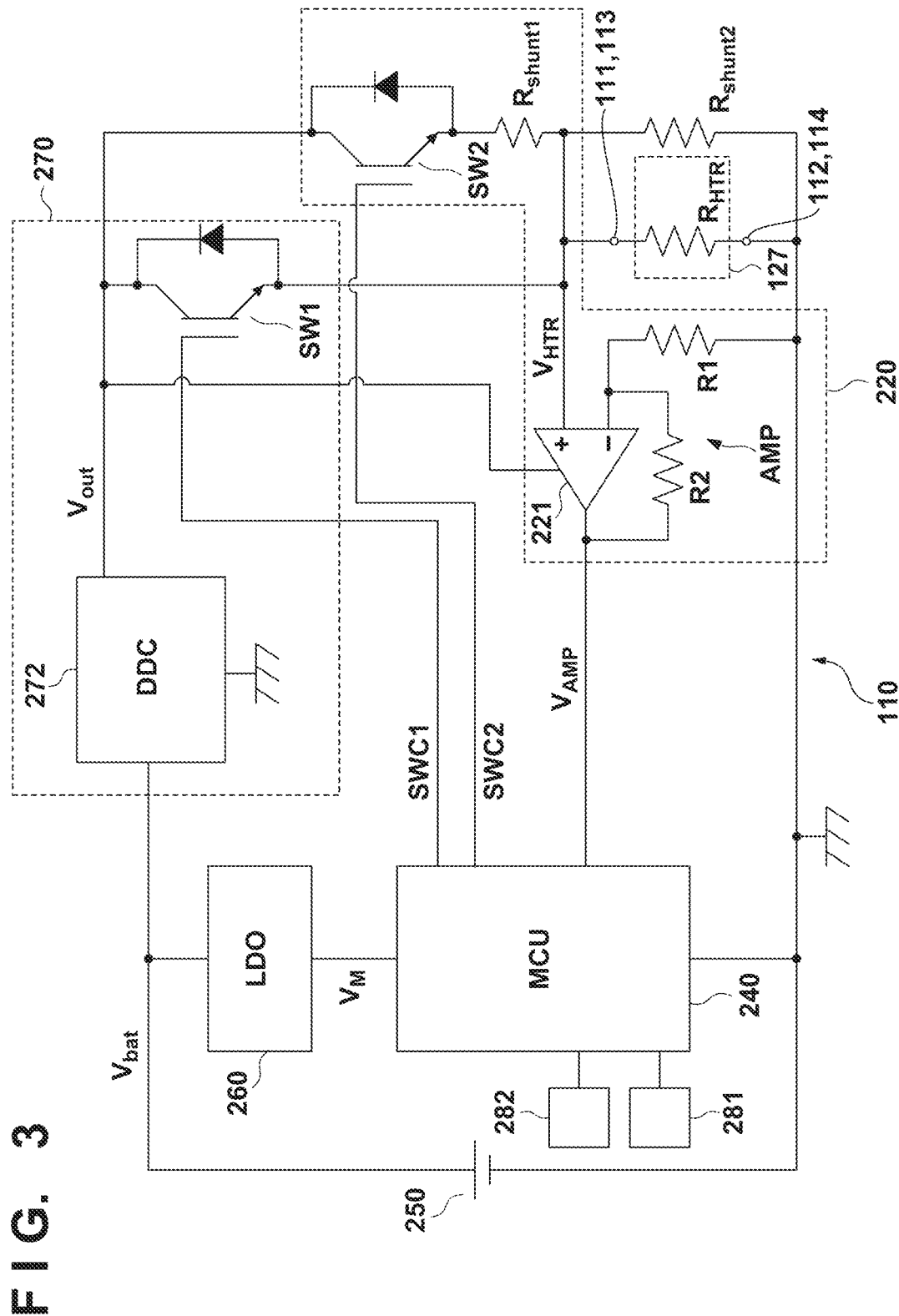
FIG. 3 is a view showing the second arrangement example of the electric component.

FIG. 3 is a view showing the second arrangement example of the electric component 110. The second arrangement example is different from the first arrangement example in that a shunt resistor (second resistive element) $R_{shunt2}$ is provided, in series with the shunt resistor $R_{shunt1}$, between a shunt resistor $R_{shunt1}$ and the ground line, and the rest is the same as in the first arrangement example. The shunt resistor $R_{shunt2}$ is a resistive element that electrically connects the first electrical contact 111 and the second electrical contact 112. Here, the resistance value of the shunt resistor $R_{shunt2}$ will be expressed as $R_{shunt2}$, like the reference symbol. The resistance value $R_{shunt2}$ is sufficiently larger than the resistance value $R_{HTR}$. Hence, equation (2) can be used in the calculation of the resistance value $R_{HTR}$.

Figure 4:
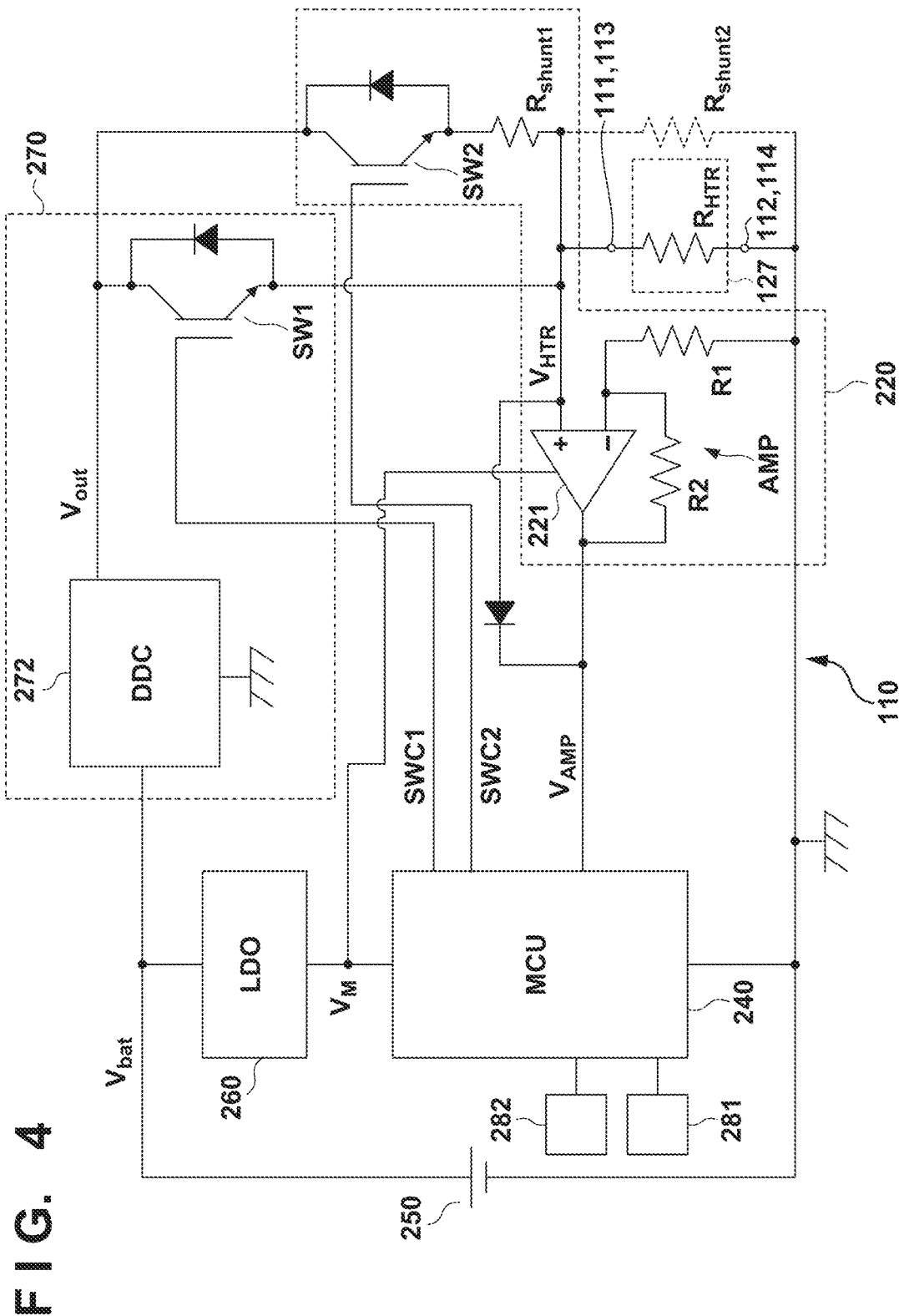
FIG. 4 is a view showing the third arrangement example of the electric component.

FIG. 4 is a view showing the third arrangement example of the electric component 110. The third arrangement example is different from the first arrangement example in that the voltage $V_M$ is supplied to the power supply terminal of the differential amplifier 221. The shunt resistor $R_{shunt2}$ as in the second arrangement example may be added to the third arrangement example, as indicated by a dotted line. Between the noninverting input terminal and the output terminal of the differential amplifier 221, a diode can be arranged in the forward direction from the noninverting input terminal to the output terminal.

Figure 5A:
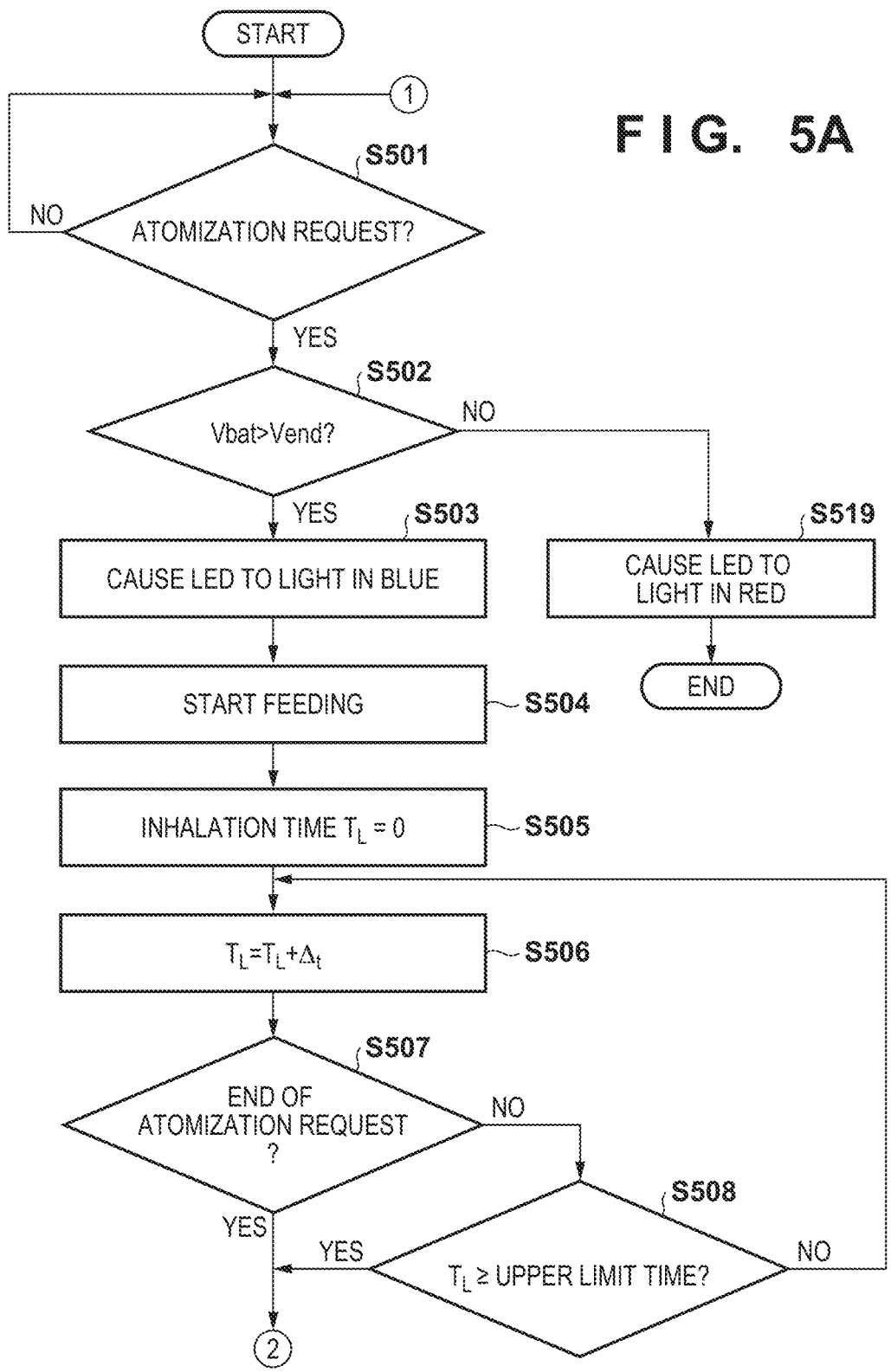
FIGS. 5A and 5B show a flowchart showing the operation of the inhalation device according to an embodiment.
Figure 5B:
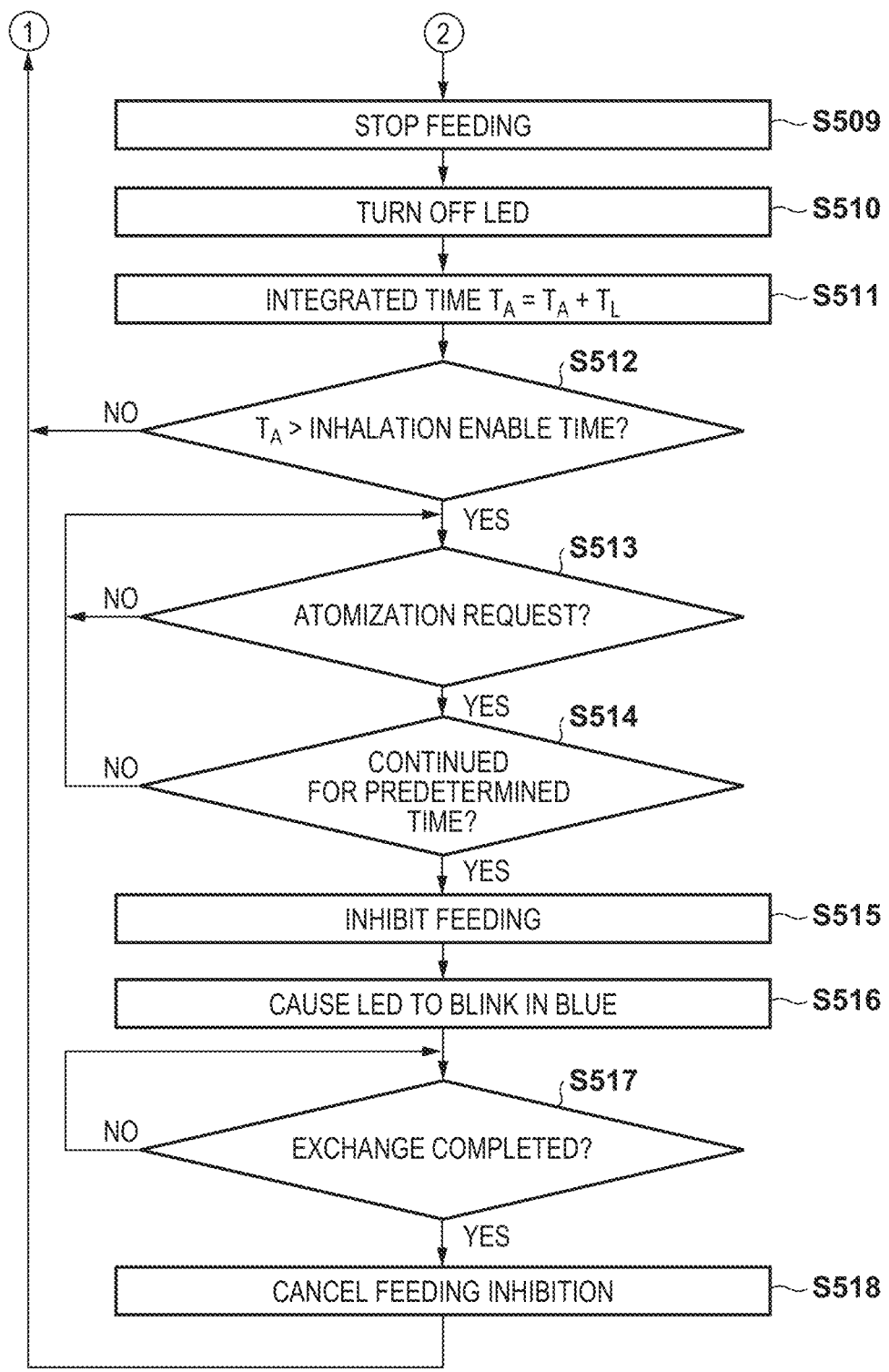

FIGS. 5A and 5B show the operation of the inhalation device 100. This operation is controlled by the processor 240. The processor 240 includes a memory that stores a program, and a CPU that operates in accordance with the program. In step S501, the processor 240 waits for reception of an atomization request, and upon receiving an atomization request, executes step S502. The atomization request is a request for operating the atomizer 104, more specifically, controlling the heater 127 within a target temperature range to generate an aerosol from the aerosol source. The atomization request can be an operation of detecting, by the puff sensor 281, that the user has performed the inhalation operation (puff operation) via the mouthpiece portion 130, and notifying, by the puff sensor 281, the processor 240 of the detection. Alternatively, the atomization request can be an operation of notifying, by the operation unit OP, the processor 240 that the user has operated the operation unit OP.

In step S502, the processor 240 acquires the power supply voltage $V_{bat}$ from a power supply management circuit (not shown), and determines whether the power supply voltage $V_{bat}$ is higher than a discharge end voltage $V_{end}$ (for example, 3.2 V). That the power supply voltage $V_{bat}$ is equal to or lower than the discharge end voltage $V_{end}$ means that the remaining dischargeable amount of the power supply 250 is not sufficient. Hence, if the power supply voltage $V_{bat}$ is equal to or lower than the discharge end voltage $V_{end}$, in step S519, the processor 240 makes a notification to promote charge of the power supply 250 using the display unit DISP of the user interface 116. If the display unit DISP includes an LED, this notification can be causing the LED to light in red. If the power supply voltage $V_{bat}$ is higher than the discharge end voltage $V_{end}$, in step S503, using the display unit DISP of the user interface 116, the processor 240 can make a notification representing that a normal operation is possible. If the display unit DISP includes an LED, this notification can be causing the LED to light in blue.

Next to step S503, in step S504, the processor 240 starts feed control for the heater 127. Feed control for the heater 127 includes temperature control of controlling the heater 127 within a target temperature range. Temperature control can include feedback control of detecting the temperature of the heater 127 by detecting the resistance value $R_{HTR}$ of the heater 127 and controlling opening/closing of the switch SW1 by the control signal SWC1 based on the detection result.

Next, in step S505, the processor 240 resets an inhalation time $T_L$ to 0. After that, in step S506, the processor 240 adds Δt to the inhalation time $T_L$. Δt corresponds to the time interval between execution of step S506 and the next execution of step S506.

Next, in step S507, the processor 240 determines whether the atomization request has ended. If the atomization request has ended, in step S509, the processor 240 stops feed control for the heater 127. On the other hand, if the atomization request has not ended, in step S508, the processor 240 determines whether the inhalation time T L has reached an upper limit time. If the inhalation time $T_L$ has not reached the upper limit time, the process returns to step S506. As an example, the upper limit time may be 2.0 to 2.5 sec.

Next to step S509, in step S510, the processor 240 turns off the LED that is lighting in blue. Next, in step S511, the processor 240 updates an integrated time TA. More specifically, in step S511, the inhalation time $T_L$ is added to the integrated time TA at the current point of time. The integrated time TA can be an integrated time when the capsule 106 was used for inhalation, in other words, an integrated time when the aerosol was inhaled via the flavor source 131 of the capsule 106.

In step S512, the processor 240 determines whether the integrated time TA is not more than an inhalation enable time (for example, 120 sec). If the integrated time TA is not more than the inhalation enable time, this means that the capsule 106 can still provide the flavor substance. In this case, the process returns to step S501. If the integrated time TA is more than the inhalation enable time, in step S513, the processor 240 waits for generation of the atomization request. If the atomization request is generated, in step S514, the processor 240 waits for continuation of the atomization request for a predetermined time. After that, in step S515, the processor 240 inhibits feed control for the heater 127. Note that step S514 may be omitted.

Next, in step S516, using the display unit DISP of the user interface 116, the processor 240 can make a notification to promote exchange of the capsule 106. If the display unit DISP includes an LED, this notification can be causing the LED to blink in blue (repeat on/off). Hence, the user can exchange the capsule 106. In an example, one atomizer 104 and a plurality of (for example, three) capsules 106 can be sold as one set. In this example, after one atomizer 104 and all capsules 106 in one set are consumed, the atomizer 104 and the last capsule 106 in the consumed set can be exchanged with an atomizer 104 and a capsule 106 of a new set.

In step S517, the processor 240 waits for the exchange of the capsule 106 (or the capsule 106 and the atomizer 104). In step S518, the processor 240 cancels inhibition of feed control for the heater 127 and returns to step S501.

Figure 6B:
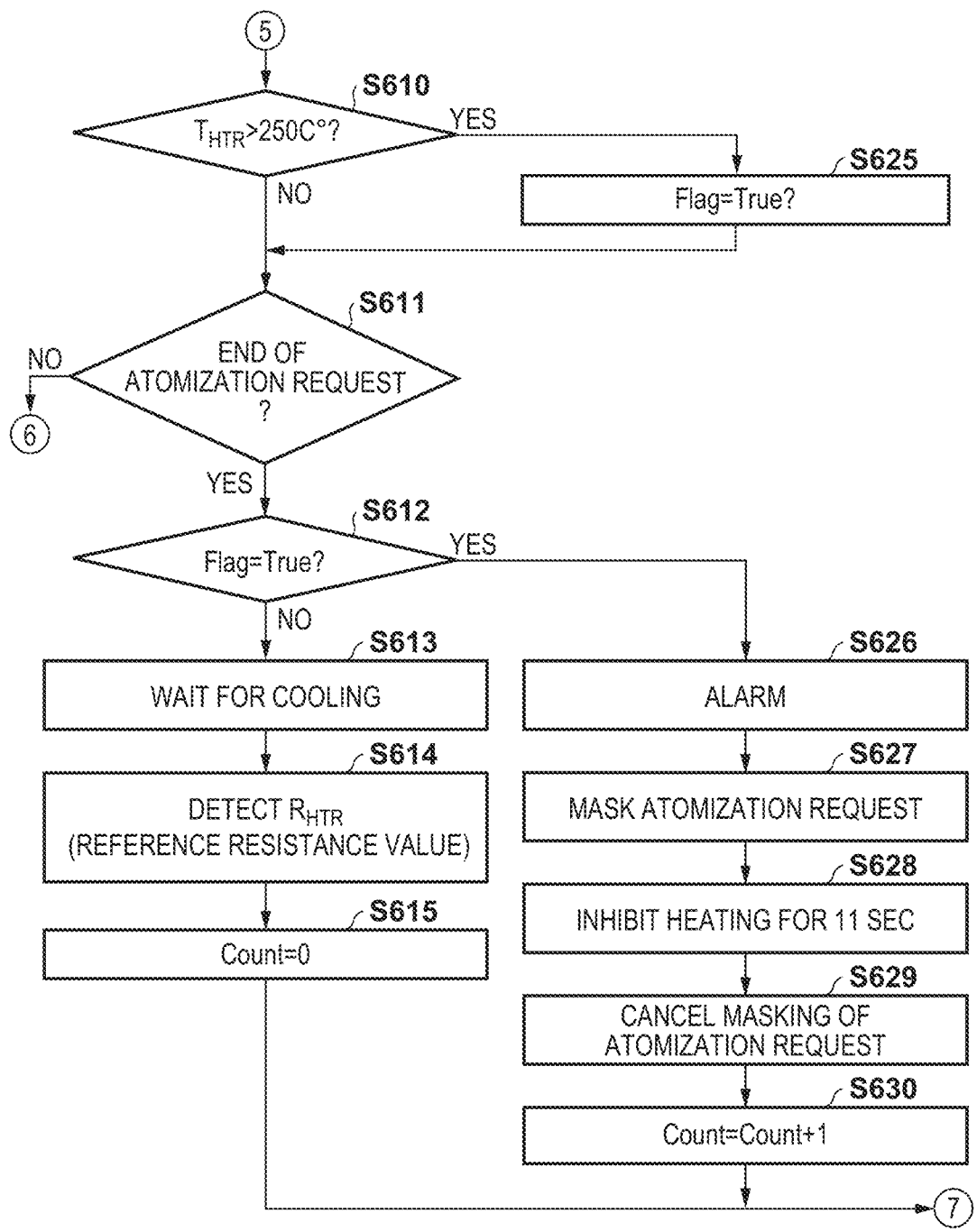

Detection associated processing concerning detection of the resistance value $R_{HTR}$ of the heater 127 and detection of the temperature of the heater 127 based on that will be described below. FIGS. 6A and 6B show detection associated processing. Detection associated processing is executed by the processor 240 separately from the processing shown in FIGS. 5A and 5B. Feed control described with reference to FIGS. 5A and 5B can be executed based on the temperature of the heater 127 acquired by detection associated processing shown in FIGS. 6A and 6B.

In step S601, the processor 240 determines whether an atomization request is present. If an atomization request is present, the process advances to step S602. If an atomization request is not present, the process advances to step S621. In step S602, the processor 240 determines whether Count that is a variable for control is equal to or larger than a predetermined number (for example, 3). If Count is equal to or larger than the predetermined number, the process advances to step S616. Otherwise, the process advances to step S603. Count is a variable that is incremented every time it is detected that the temperature of the heater 127 exceeds 250° C. That Count is equal to or larger than the predetermined number indicates that the aerosol source in the container 125 of the atomizer 104 is nearly exhausted or is completely exhausted. The value of the predetermined number can be determined in consideration of the detection error (including the influence of noise) of the temperature of the heater 127, and the like.

Note that feed control for the heater 127 is optimized assuming a state in which the aerosol source is not exhausted (that is, an endothermic amount by the aerosol source). Hence, if the aerosol source is nearly exhausted or completely exhausted, heat generated by the heater 127 is excessive, and the temperature of the heater 127 may rise beyond the upper limit of the target temperature range.

In step S603, the processor 240 turns on the switch SW1. In step S604, the processor 240 turns on the switch SW2. Next, in step S605, the processor 240 turns off the switch SW1. In this state, the resistance value $R_{HTR}$ of the heater 127 can be detected. In step S606, the processor 240 calculates the resistance value $R_{HTR}$ of the heater 127 in accordance with equations (2) and (4) based on the output voltage $V_{AMP}$ of the amplifier AMP of the detection circuit 220.

In step S607, the processor 240 calculates the resistance value Rim of the heater 127 in accordance with equation (5) based on the resistance value $R_{HTR}$ of the heater 127 calculated in step S606 and reference temperature $T_{ref}$ and the reference resistance value $R_{ref}$ that are already set. Steps S606 and S607 correspond to processing (second processing) of acquiring the temperature of the heater 127 based on the reference resistance value $R_{ref}$ and the information obtained using the detection circuit 220. In step S608, the processor 240 turns off the switch SW2.

In step S609, the processor 240 determines whether a temperature $T_{HTR}$ of the heater 127 exceeds 300° C. If the temperature $T_{HTR}$ exceeds 300° C. (the second temperature), the process advances to step S616. If the temperature $T_{HTR}$ is equal to or lower than 300° C., the process advances to step S610. In step S610, the processor 240 determines whether the temperature $T_{HTR}$ of the heater 127 exceeds 250° C. (the first temperature). If the temperature $T_{HTR}$ exceeds 250° C., the process advances to step S625. If the temperature $T_{HTR}$ is equal to or lower than 250° C., the process advances to step S611. In step S625, the processor 240 sets a flag Flag (that is, Flag=true). In this example, that the temperature $T_{HTR}$ of the heater 127 exceeds 250° C. (first temperature) indicates that the aerosol source in the container 125 of the atomizer 104 is nearly exhausted. That the temperature $T_{HTR}$ of the heater 127 exceeds 300° C. (second temperature) indicates that the aerosol source is completely exhausted. However, the first temperature and the second temperature can arbitrarily be determined in accordance with the type of the aerosol source, the structure of the transport portion (wick) 126, and the like.

In step S611, the processor 240 determines whether the atomization request has ended. If the atomization request has ended, the process advances to step S612. If the atomization request has not ended, the process returns to step S603. In step S612, the processor 240 determines whether the flag Flag is set. If the flag Flag is set, the process advances to step S626. If the flag Flag is not set, the process advances to step S613. That the flag Flag is set indicates that the temperature $T_{HTR}$ of the heater 127 exceeds 250° C.

In step S613, the processor 240 waits for completion of natural cooling of the heater 127. As for the completion of natural cooling of the heater 127, the resistance value $R_{HTR}$ of the heater 127 is detected, and the completion can be determined based on the temperature of the heater 127 calculated based on the resistance value $R_{HTR}$. Alternatively, the elapse of a preset time may be waited, thereby determining that the natural cooling of the heater 127 is completed.

Next to step S613, in step S614, the processor 240 turns on the switch SW2, detects the output voltage $V_{AMP}$ of the amplifier AMP, and after that, turns off the switch SW2. Also, in step S614, the processor 240 calculates the resistance value $R_{HTR}$ of the heater 127 in accordance with equations (2) and (4) based on the detected output voltage $V_{AMP}$. The resistance value $R_{HTR}$ at this time is the resistance value of the heater 127 in a state in which the heater 127 is sufficiently naturally cooled, and therefore, can be used as the reference resistance value $R_{ref}$. The temperature at this time can be used as the reference temperature $T_{ref}$, and as the temperature, for example, a temperature provided from the temperature sensor 282 can be used. In step S614, the processor 240 stores the acquired reference resistance value $R_{ref}$ and the reference temperature $T_{ref}$ in the memory. In step S615, the processor 240 resets Count to 0.

If the processor 240 determines in step S609 that the temperature $T_{HTR}$ of the heater 127 exceeds 300° C., in step S616, the processor 240 makes a notification representing the occurrence of an abnormality (exhaustion of the aerosol source) using the display unit DISP of the user interface 116. If the display unit DISP includes an LED, this notification can be causing the LED to blink in red (repeat on/off).

Next, in step S617, the atomization request is masked (disabled). In a state in which the atomization request is masked, even if an atomization request is generated, it is ignored. That is, in a state in which the atomization request is masked, even if an atomization request is generated, it is determined in step S601 (also in step S501 of FIGS. 5A and 5B) that the atomization request does not exist. Next, in step S618, the processor 240 determines whether the time (non-operation time) in which an operation by the user on the operation unit OP of the user interface 116 is not performed has reached a predetermined time (for example, 6 min). If the non-operation time has reached the predetermined time, the processor 240 transitions to a sleep state. Return from the sleep state can be done in response to, for example, an operation by the user on the operation unit OP of the user interface 116.

Until the non-operation time reaches the predetermined time, step S619 is executed. In step S619, the processor 240 waits for completion of the exchange work of the atomizer 104. More specifically, in step S619, the processor 240 waits for an operation of detaching the atomizer 104 from (the holding portion 103 of) the controller 102 and attaching a new atomizer 104 to (the holding portion 103 of) the controller 102. The processor 240 can determine completion of the exchange work of the atomizer 104 based on a change in the output voltage $V_{AMP}$ of the amplifier AMP of the detection circuit 220.

Here, when the atomizer 104 is detached from the holding portion 103, the heater 127 connected between the first electrical contact 111 and the second electrical contact 112 is lost. Hence, the output voltage $V_{AMP}$ of the amplifier AMP changes. Based on this, the processor 240 can detect the detachment of the atomizer 104 from the holding portion 103. When the atomizer 104 is attached to the holding portion 103, the heater 127 connected between the first electrical contact 111 and the second electrical contact 112 is connected. Hence, the output voltage $V_{AMP}$ of the amplifier AMP changes. Based on this, the processor 240 can detect that the atomizer 104 is attached to the holding portion 103.

Upon detecting the exchange of the atomizer 104, in step S620, the processor 240 resets Count to 0 and clears Flag. Next, in step S621, the processor 240 detects the output voltage $V_{AMP}$ of the amplifier AMP, calculates the resistance value $R_{HTR}$ of the heater 127 in accordance with equations (2) and 4 based on the output voltage $V_{AMP}$, and stores the resistance value $R_{HTR}$ in the memory as the reference resistance value $R_{ref}$. Step S621 is processing (first processing) of acquiring the reference resistance value in accordance with exchange of the atomizer 104 or in accordance with transition from a non-holding state in which the atomizer 104 is not held by the holding portion 103 to a holding state in which the atomizer 104 is held by the holding portion 103.

The resistance value $R_{HTR}$ detected in step S621 is the resistance value of the heater 127 to which power is not fed (unheated) and can therefore be used as the reference resistance value $R_{ref}$. However, as will be described later, the output voltage $V_{AMP}$ of the detection circuit 220 can vary due to an operation of applying stress between the electrical contact of the controller 102 and the electrical contact of the atomizer 104, like a work of exchanging the capsule 106. Hence, as will be described later, the processor 240 can acquire the resistance value $R_{HTR}$ of the heater 127 as the reference resistance value $R_{ref}$ in accordance with a smoothed signal generated by smoothing information (output voltage $V_{AMP}$) obtained using the detection circuit 220. In addition, the processor 240 can detect the temperature of the heater 127 using the thus acquired reference resistance value $R_{ref}$ and generate a control signal (for example, the control signal SWC1 that controls the switch SW1 or a control signal that controls the display unit DISP) based on the temperature. That is, the processor 240 can generate a control signal in accordance with a smoothed signal generated by smoothing information obtained using the detection circuit 220.

In step S622, the processor 240 acquires the temperature of a predetermined portion of the inhalation device 100 from the temperature sensor 282, and stores the temperature in the memory as the reference temperature $T_{ref}$.

Here, a temperature difference may exist between the heater 127 and the predetermined portion of the inhalation device 100. Such a temperature difference can be ignored. Alternatively, the processor 240 may store a temperature obtained by adding a predetermined value to the temperature acquired from the temperature sensor 282 in the memory as the reference temperature $T_{ref}$.

Next, in step S623, masking of the atomization request is canceled. The processor 240 may reverse the order to execute steps S621 and S622, and execute step S621 after step S622. The processor 240 may simultaneously execute steps S621 and S622.

In step S624, the processor 240 determines whether the non-operation time in which an operation by the user on the operation unit OP of the user interface 116 is not performed has reached a predetermined time (for example, 6 min). If the non-operation time has reached the predetermined time, the processor 240 transitions to the sleep state. On the other hand, until the non-operation time reaches the predetermined time, the processor 240 returns to step S601.

In step S626, the processor 240 makes a notification representing the occurrence of an abnormality (exhaustion of the aerosol source) using the display unit DISP of the user interface 116. If the display unit DISP includes an LED, this notification can be causing the LED to blink in red (repeat on/off). Next, in step S627, the processor 240 masks (disables) the atomization request. In step S628, the processor 240 inhibits heating of the heater 127 (feeding to the heater 127) for a predetermined period (for example, 11 sec). Next, in step S629, masking of the atomization request is canceled. In step S630, the processor 240 increments Count and returns to step S618.

Figure 7:
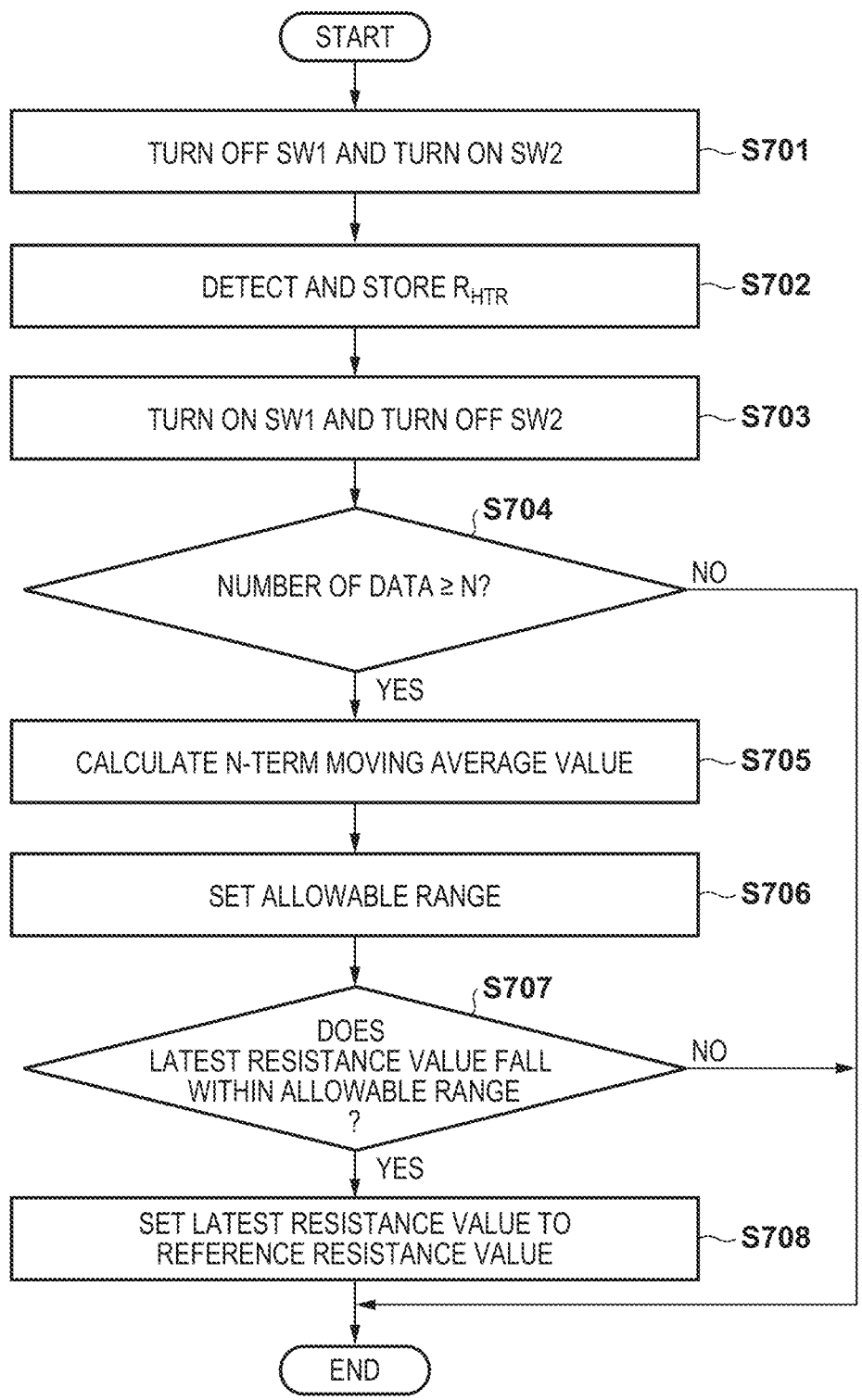
FIG. 7 is a flowchart showing the first example for providing details of detection processing of a reference resistance value.

FIG. 7 shows the first example for providing details of detection processing of the reference resistance value in step S621 of FIGS. 6A and 6B. In step S701, the processor 240 turns off the switch SW1, and turns on the switch SW2. In step S702, the processor 240 detects the output voltage $V_{AMP}$ of the amplifier AMP of the detection circuit 220, calculates the resistance value $R_{HTR}$ of the heater 127 in accordance with equations (2) and (4) based on the detected output voltage $V_{AMP}$, and stores data representing the resistance value $R_{HTR}$ in the working area of the memory. In step S703, the processor 240 turns on the switch SW1, and turns off the switch SW2.

In step S704, the processor 240 determines whether the number of data representing the resistance values $R_{HTR}$ stored in the working area in step S702 is equal to or larger than N (preset natural number). If the number of data is equal to or larger than N, the process advances to step S705. Otherwise, the processing shown in FIG. 7 is ended. In step S705, the processor 240 calculates the average value (that is, an N-term moving average value) of N latest data in the plurality of data representing the resistance values $R_{HTR}$ stored in the working area in step S702.

In step S706, the processor 240 sets, as an allowable range, a range in which the deviation amount from the N-term moving average value calculated in step S705 equals a threshold |ΔR|, that is, the range of N-term moving average value ±ΔR. In step S707, the processor 240 determines whether latest data in the plurality of data representing the resistance values $R_{HTR}$ stored in the working area in step S702 falls within the allowable range set in step S706. If the latest data falls within the allowable range, in step S708, the processor 240 stores the latest data in the memory as the reference resistance value $R_{ref}$. This means that the reference resistance value $R_{ref}$ already stored in the memory is updated by the new reference resistance value $R_{ref}$. On the other hand, if the latest data does not fall within the allowable range, or if the number of data is not equal to or larger than N, the processor 240 does not execute step S708. In this case, the reference resistance value $R_{ref}$ already stored in the memory is not updated.

According to the first example, the processor 240 calculates the N-term moving average value of the information (resistance value $R_{HTR}$) sequentially obtained using the detection circuit 220, and uses, as the smoothed signal, information whose deviation amount from the N-term moving average value is equal to or smaller than a threshold in the information (resistance value $R_{HTR}$) sequentially obtained using the detection circuit 220. Here, use of the moving average value is an example of a method using an average value. For example, the average value may be calculated for every predetermined number of continuous data, and the allowable range may be set based on the average value.

Figure 8:
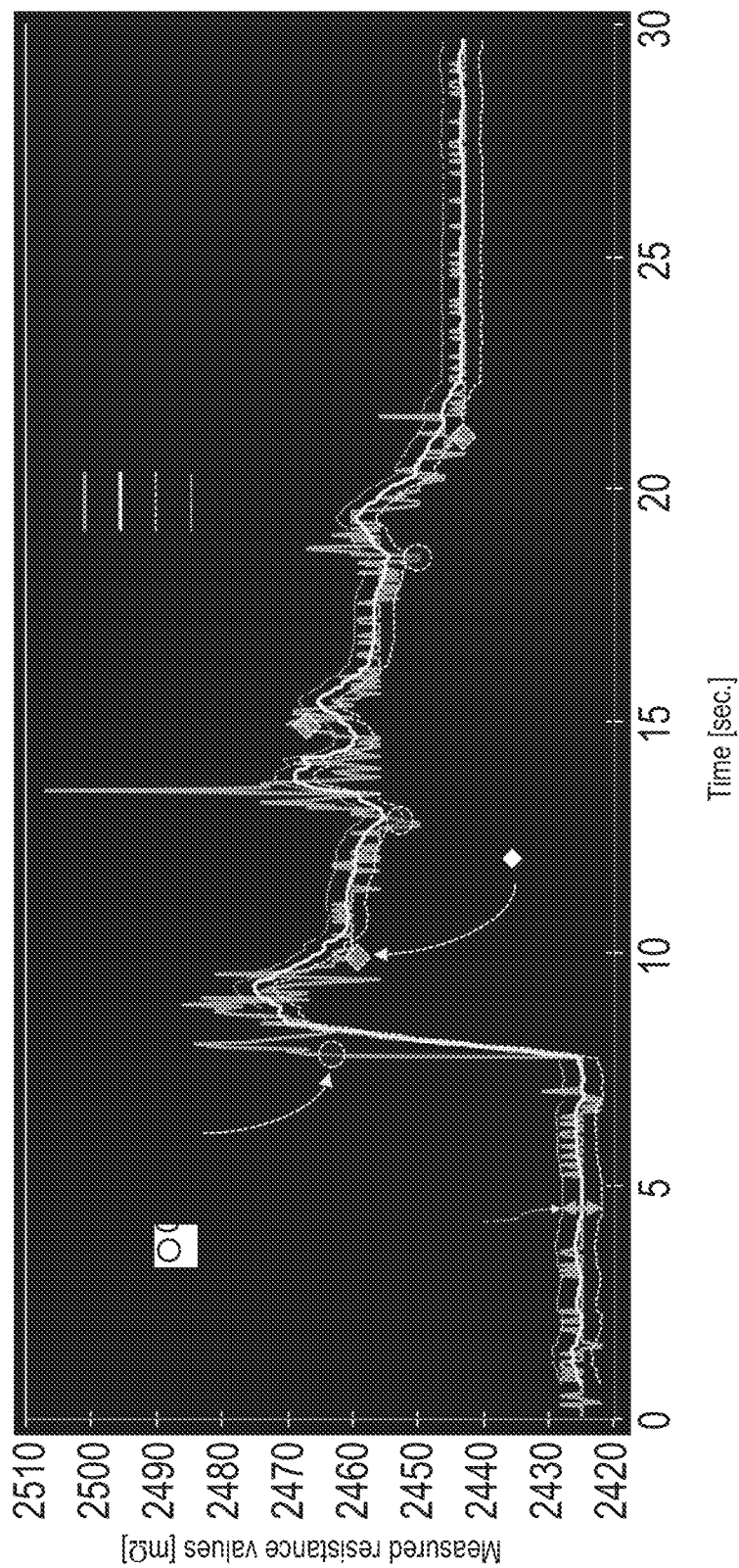
FIG. 8 is a view showing a result of verifying the usefulness of the first example shown in FIG. 7.

FIG. 8 shows a result of verifying the usefulness of the first example shown in FIG. 7. In the example shown in FIG. 8, N=15. "Measured resistance values" represent the data of the resistance values $R_{HTR}$ sequentially obtained using the detection circuit 220. "15-term moving average value" is the 15-term moving average value of "Measured resistance values". "15-term moving average value −3 mΩ" represents the lower limit of the allowable range decided based on the 15-term moving average value, and "15-term moving average value +3 mΩ" represents the upper limit of the allowable range decided based on the 15-term moving average value. A circular mark ("capsule attachment") represents a variation in the resistance value $R_{HTR}$ caused by the attachment of the capsule 106 to (the capsule holder 105 of) the atomizer 104. A diamond mark ("capsule detachment") represents a variation in the resistance value $R_{HTR}$ caused by the detachment of the capsule 106 from (the capsule holder 105 of) the atomizer 104. In other words, attachment of the capsule 106 to (the capsule holder 105 of) the atomizer 104 is performed at the timing of the circular mark ("capsule attachment"). Similarly, detachment of the capsule 106 from (the capsule holder 105 of) the atomizer 104 is performed at the timing of the diamond mark ("capsule detachment"). It is found that the resistance value R HTR can greatly vary due to the detachment and attachment of the capsule 106.

According to the first example, of the resistance values $R_{HTR}$ sequentially obtained using the detection circuit 220, the resistance value $R_{HTR}$ that falls within the allowable range decided based on the moving average value (average value) is used as the smoothed signal, and the reference resistance value $R_{ref}$ is decided based on the smoothed signal. It is therefore possible to accurately set the reference resistance value $R_{ref}$. Hence, at the time of detection of the temperature of the heater 127, the temperature can accurately be detected. In addition, the control signal to be generated based on the temperature can accurately be generated.

Figure 9:
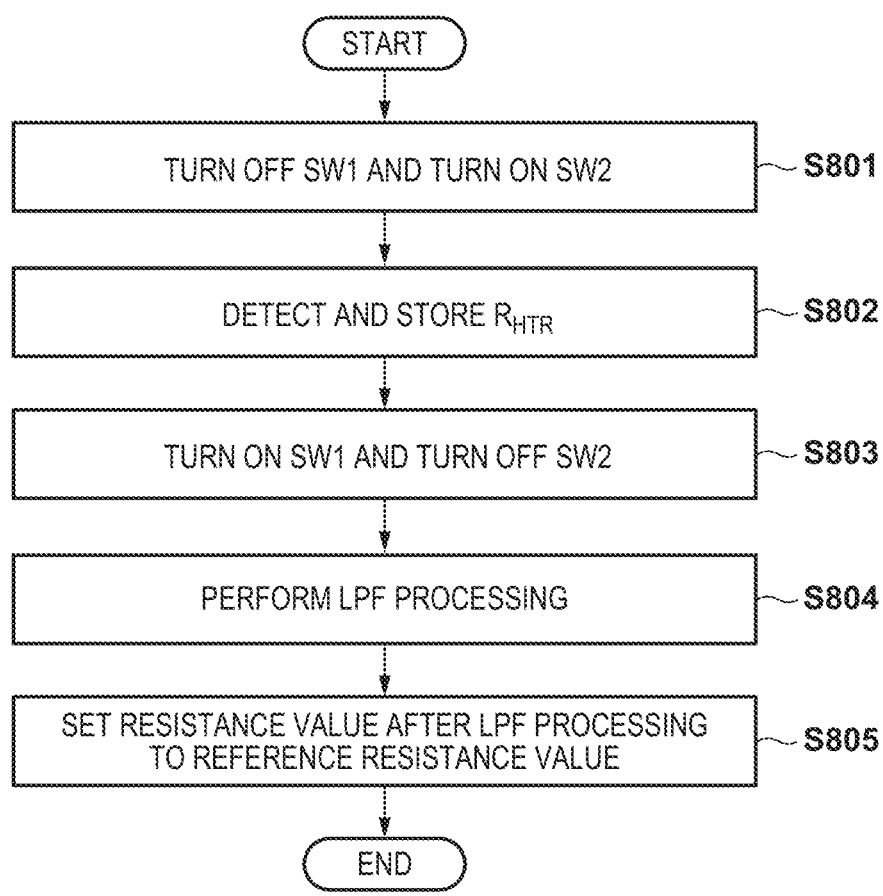
FIG. 9 is a flowchart showing the second example for providing details of detection processing of the reference resistance value.

FIG. 9 shows the second example for providing details of detection processing of the reference resistance value in step S621 of FIGS. 6A and 6B. In step S801, the processor 240 turns off the switch SW1, and turns on the switch SW2. In step S802, the processor 240 detects the output voltage $V_{AMP}$ of the amplifier AMP of the detection circuit 220, calculates the resistance value $R_{HTR}$ of the heater 127 in accordance with equations (2) and (4) based on the detected output voltage $V_{AMP}$, and stores data representing the resistance value $R_{HTR}$ in the working area of the memory. In step S803, the processor 240 turns on the switch SW1, and turns off the switch SW2.

In step S804, the processor 240 performs LPF (Low Pass Filter) processing for the resistance value $R_{HTR}$ stored in the working area in step S802, thereby generating a smoothed signal by smoothing the resistance value $R_{HTR}$ stored in the working area. In step S805, the processor 240 stores the resistance value after the LPF processing in step S804, that is, the resistance value represented by the smoothed signal in the memory as the reference resistance value $R_{ref}$.

Figure 11:
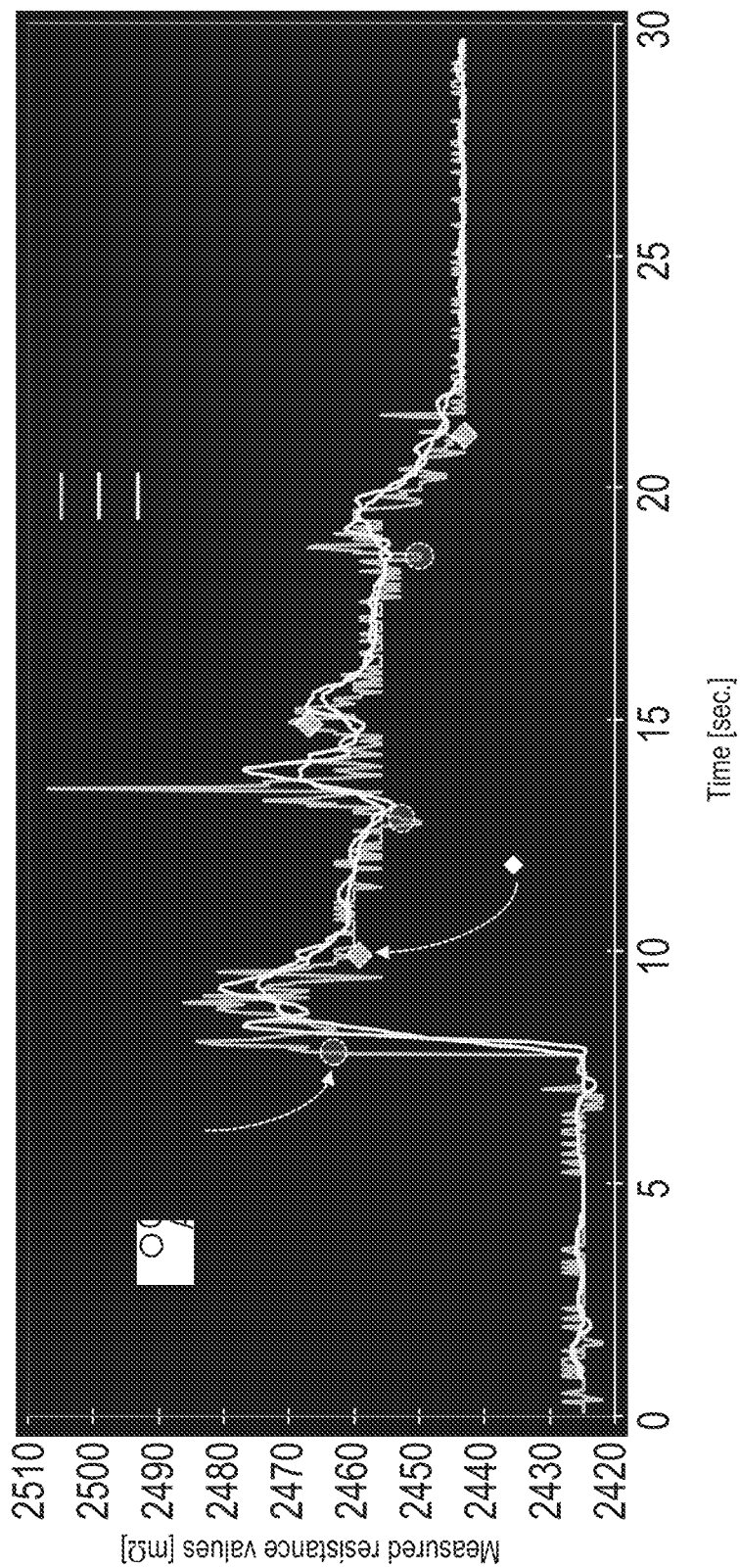
FIG. 11 is a view showing a result of verifying the usefulness of the second and third examples shown in FIGS. 9 and 10.

FIG. 11 shows a result of verifying the usefulness of the second example shown in FIG. 9. "Measured resistance values" represent the data of the resistance values $R_{HTR}$ sequentially obtained using the detection circuit 220. "Processed by LPF" represents a result of performing LPF processing for "Measured resistance values". According to the second example, the result of performing LPF processing for the resistance value $R_{HTR}$ sequentially obtained using the detection circuit 220 is used as a smoothed signal, and the reference resistance value $R_{ref}$ is decided based on the smoothed signal. It is therefore possible to accurately set the reference resistance value $R_{ref}$. Hence, at the time of detection of the temperature of the heater 127, the temperature can accurately be detected. In addition, the control signal to be generated based on the temperature can accurately be generated.

Figure 10:
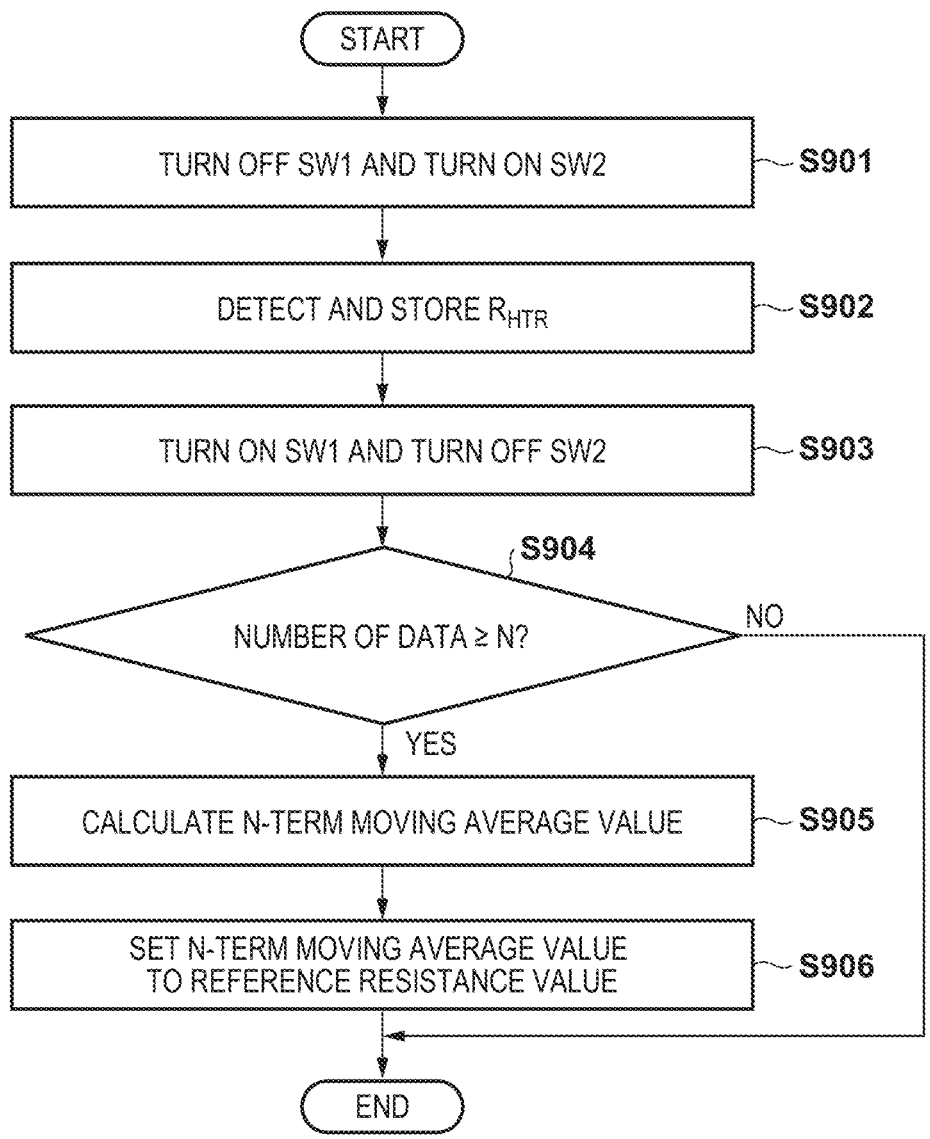
FIG. 10 is a flowchart showing the third example for providing details of detection processing of the reference resistance value.

FIG. 10 shows the third example for providing details of detection processing of the reference resistance value in step S621 of FIGS. 6A and 6B. In step S901, the processor 240 turns off the switch SW1, and turns on the switch SW2. In step S902, the processor 240 detects the output voltage $V_{AMP}$ of the amplifier AMP of the detection circuit 220, calculates the resistance value $R_{HTR}$ of the heater 127 in accordance with equations (2) and (4) based on the detected output voltage $V_{AMP}$, and stores data representing the resistance value $R_{HTR}$ in the working area of the memory. In step S903, the processor 240 turns on the switch SW1, and turns off the switch SW2.

In step S904, the processor 240 determines whether the number of data representing the resistance values $R_{HTR}$ stored in the working area in step S902 is equal to or larger than N (preset natural number). If the number of data is equal to or larger than N, the process advances to step S905. Otherwise, the processing shown in FIG. 10 is ended. In step S905, the processor 240 calculates the average value (that is, an N-term moving average value) of N latest data in the plurality of data representing the resistance values $R_{HTR}$ stored in the working area in step S902.

In step S906, the processor 240 stores the N-term moving average value calculated in step S905 in the memory as the reference resistance value $R_{ref}$. This means that the reference resistance value $R_{ref}$ already stored in the memory is updated by the new reference resistance value $R_{ref}$. On the other hand, if the number of data is not equal to or larger than N, the processor 240 does not execute step S906. In this case, the reference resistance value $R_{ref}$ already stored in the memory is not updated.

Referring back to FIG. 11, FIG. 11 shows a result of verifying the usefulness of the third example shown in FIG. 10. "Measured resistance values" represent the data of the resistance values $R_{HTR}$ sequentially obtained using the detection circuit 220. "16-term moving average" is the 16-term moving average of "Measured resistance values". According to the third example, the moving average value of the resistance values $R_{HTR}$ sequentially obtained using the detection circuit 220 is used as a smoothed signal, and the reference resistance value $R_{ref}$ is decided based on the smoothed signal. It is therefore possible to accurately set the reference resistance value $R_{ref}$. Hence, at the time of detection of the temperature of the heater 127, the temperature can accurately be detected. In addition, the control signal to be generated based on the temperature can accurately be generated.

Figure 12:
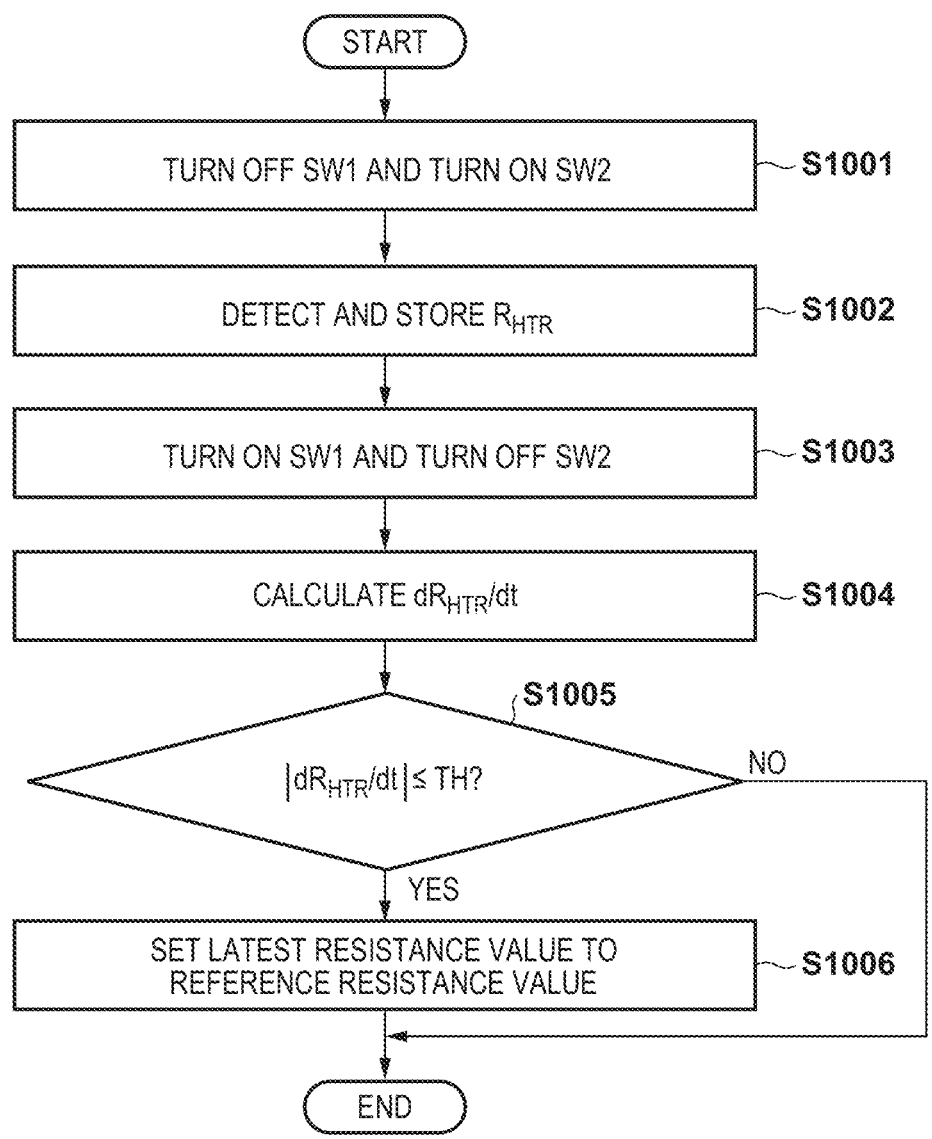
FIG. 12 is a flowchart showing the fourth example for providing details of detection processing of the reference resistance value.

FIG. 12 shows the fourth example for providing details of detection processing of the reference resistance value in step S621 of FIGS. 6A and 6B. In step S1001, the processor 240 turns off the switch SW1, and turns on the switch SW2. In step S1002, the processor 240 detects the output voltage $V_{AMP}$ of the amplifier AMP of the detection circuit 220, calculates the resistance value $R_{HTR}$ of the heater 127 in accordance with equations (2) and (4) based on the detected output voltage $V_{AMP}$, and stores data representing the resistance value $R_{HTR}$ in the working area of the memory. In step S1003, the processor 240 turns on the switch SW1, and turns off the switch SW2.

In step S1004, the processor 240 calculates the differential value $(dR_{HTR}/dt)$ of the data representing the resistance value $R_{HTR}$ stored in the working area in step S1002. In step S1005, the processor 240 determines whether the differential value calculated in step S1005 is equal to or smaller than a threshold TH. If the latest data is equal to or smaller than the threshold TH, in step S1006, the processor 240 stores the latest data in the memory as the reference resistance value $R_{ref}$. This means that the reference resistance value $R_{ref}$ already stored in the memory is updated by the new reference resistance value $R_{ref}$. On the other hand, if the latest data is not equal to or smaller than the threshold TH, the processor 240 does not execute step S1006. In this case, the reference resistance value $R_{ref}$ already stored in the memory is not updated. The fourth example can be understood as a method of removing the peak value of the data using the differential value of the data representing the resistance value $R_{HTR}$.

Figure 13:
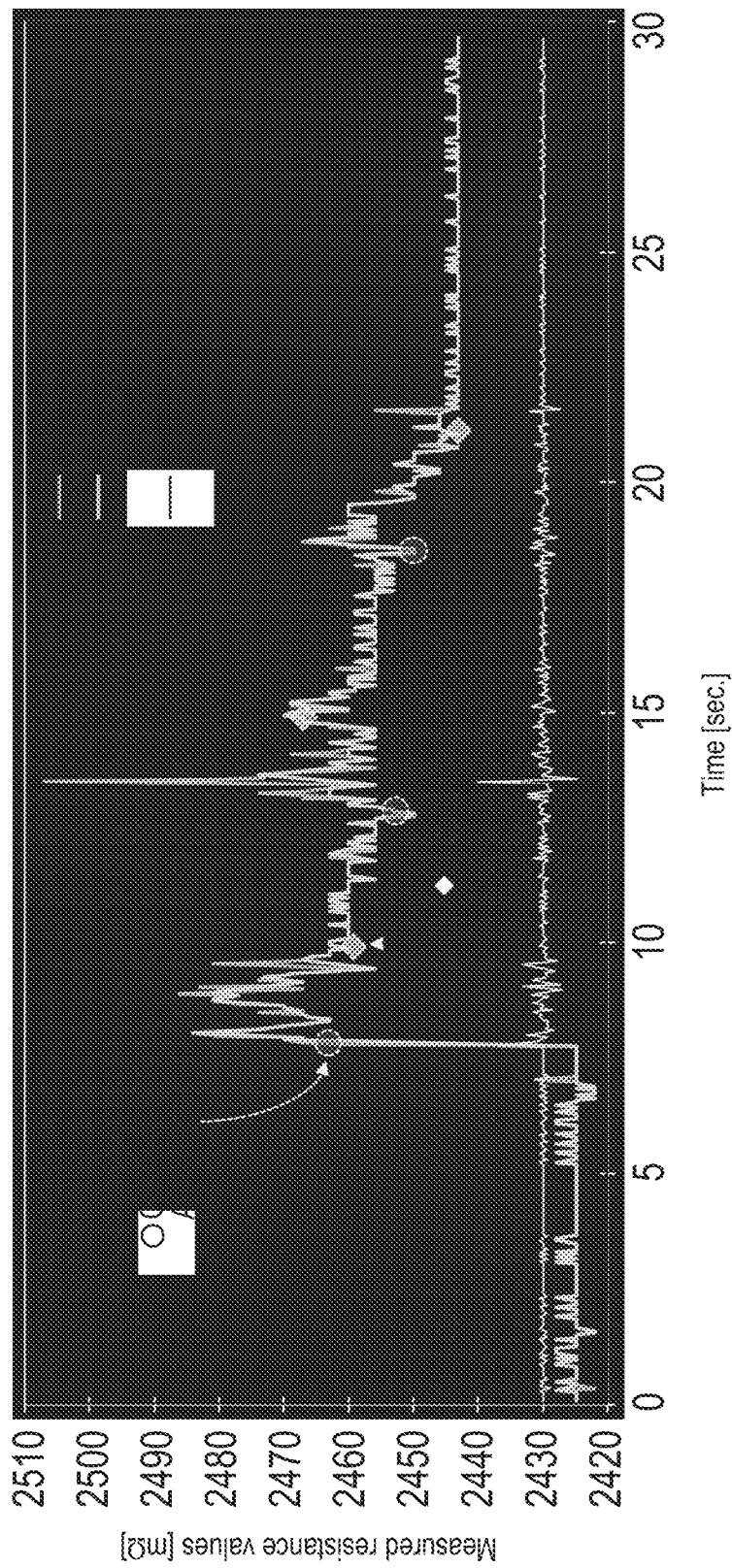
FIG. 13 is a view showing a result of verifying the usefulness of the fourth example shown in FIG. 12.

FIG. 13 shows a result of verifying the usefulness of the fourth example shown in FIG. 12. "Measured resistance values" represent the data of the resistance values $R_{HTR}$ sequentially obtained using the detection circuit 220. "Differential value" is the differential value of "Measured resistance values". "Peak removal using differential value" is data obtained by removing values whose differential values are equal to or smaller than the threshold TH, that is, the peak in "Measured resistance values". According to the fourth example, the differential value of the resistance values $R_{HTR}$ sequentially obtained using the detection circuit 220 is sequentially calculated, information representing the resistance value $R_{HTR}$ whose differential value falls within a predetermined range in the information sequentially obtained using the detection circuit 220 is used as a smoothed signal, and the reference resistance value $R_{ref}$ is decided based on the smoothed signal. It is therefore possible to accurately set the reference resistance value $R_{ref}$. Hence, at the time of detection of the temperature of the heater 127, the temperature can accurately be detected. In addition, the control signal to be generated based on the temperature can accurately be generated.

The above-described first, second, third, and fourth examples may be applied to detect the reference resistance value in step S614.

Figure 14:
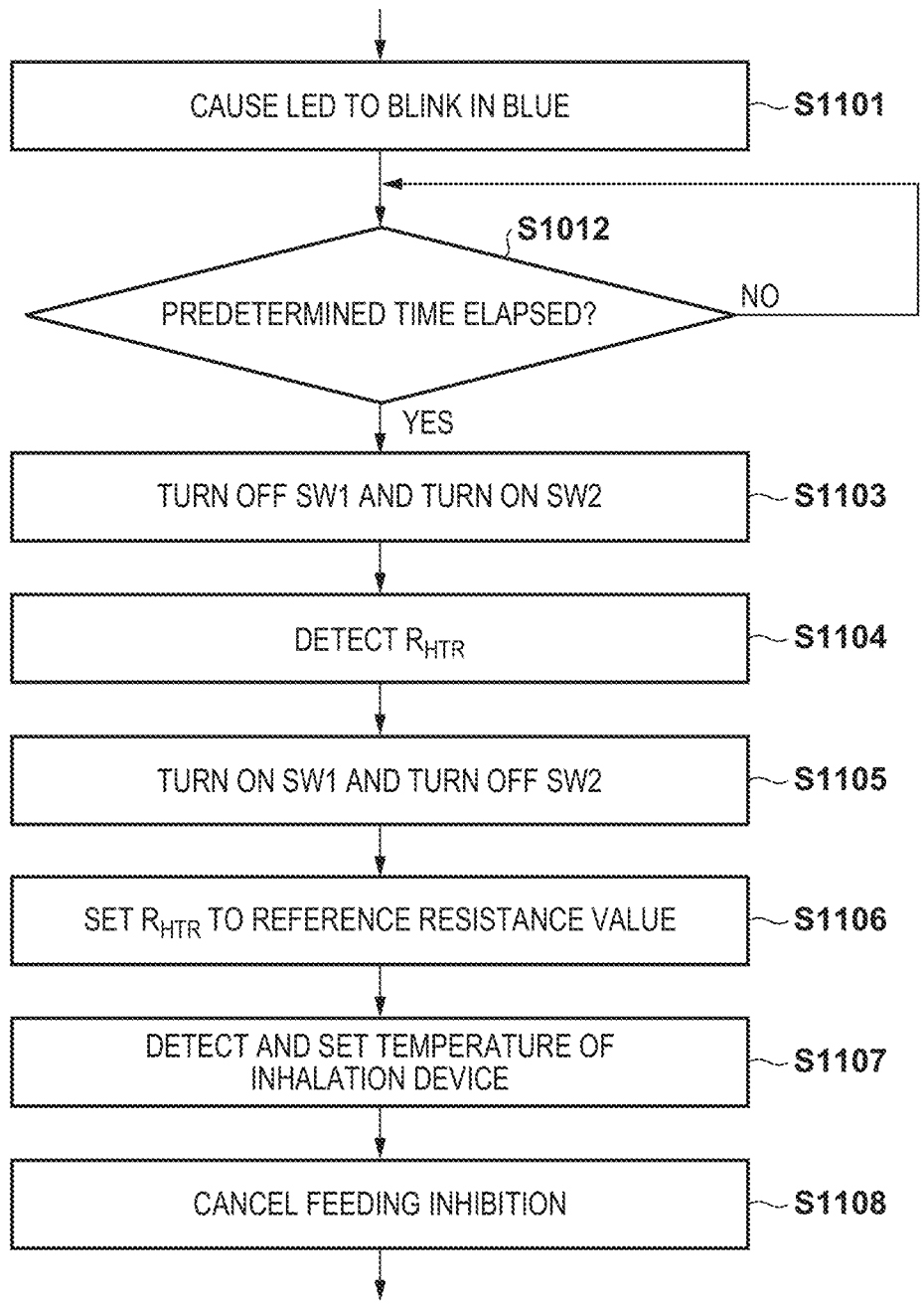
FIG. 14 is a flowchart showing a modification of the operation of the inhalation device according to an embodiment shown in FIGS. 5A and 5B.

FIG. 14 shows an example in which processing of updating the reference resistance value is included in the operation shown in FIGS. 5A and 5B. Steps S516, S517, and S518 in FIGS. 5A and 5B are replaced with steps S1101 to S1108 in FIG. 14. In step S1101, using the display unit DISP of the user interface 116, the processor 240 makes a notification to promote exchange of the capsule 106. If the display unit DISP includes an LED, this notification can be causing the LED to blink in blue (repeat on/off). Hence, the user can exchange the capsule 106. In an example, one atomizer 104 and a plurality of (for example, five) capsules 106 can be sold as one set. In this example, one atomizer 104 and all capsules 106 in one set are consumed, and the atomizer 104 and the last capsule 106 in the consumed set can be exchanged with an atomizer 104 and a capsule 106 of a new set.

Figure 15:
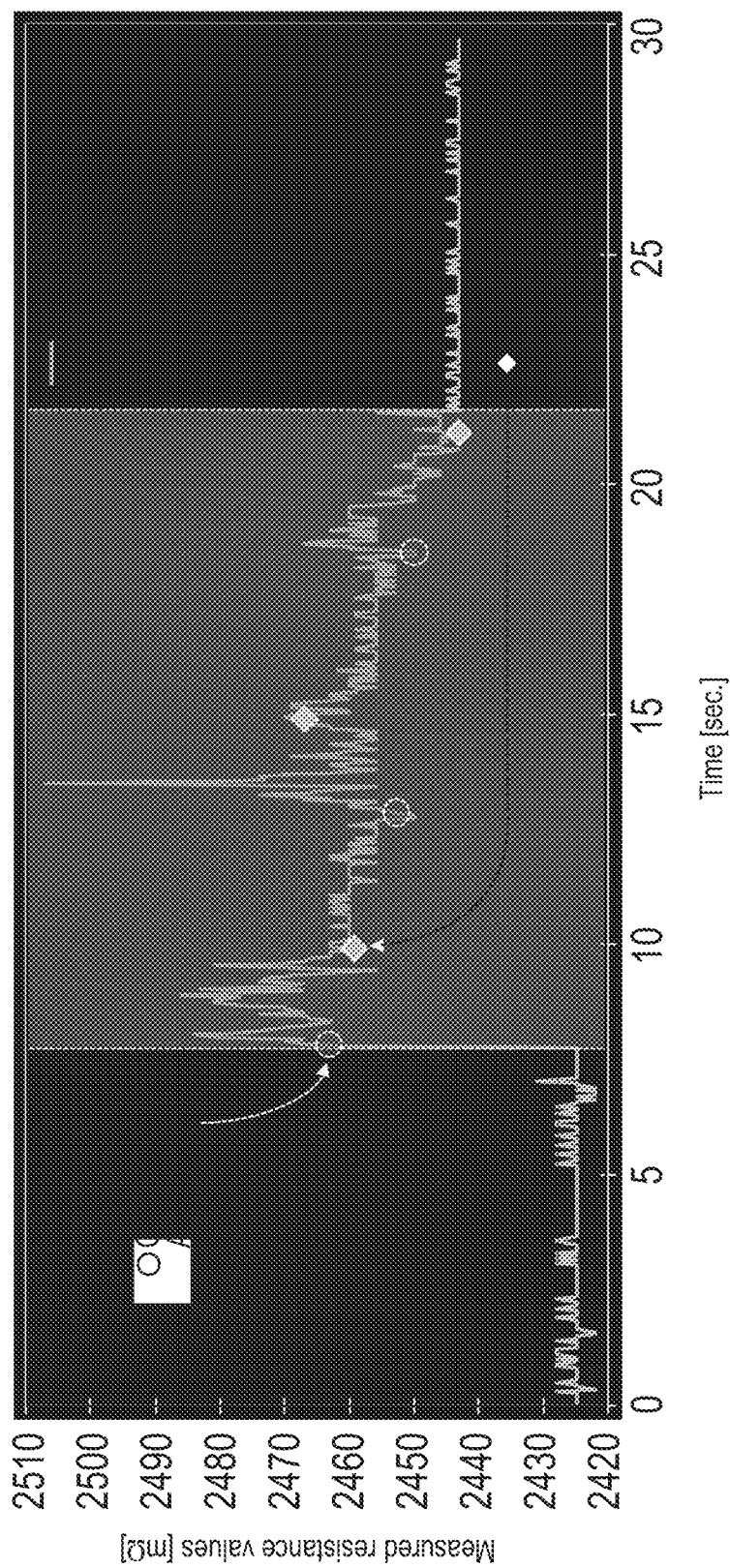
FIG. 15 is a view for explaining the usefulness of the modification shown in FIG. 14.

In step S1102, the processor 240 waits for the elapse of a predetermined time. As shown in FIG. 15, the output voltage $V_{AMP}$ of the detection circuit 220 can vary due to an operation of applying stress between the electrical contacts 111 to 114 that electrically connect the controller 102 and the atomizer 104, like a work of exchanging the capsule 106 (and/or the atomizer 104). However, in a state in which the force applied to the electrical contacts 111 to 114 that electrically connect the controller 102 and the atomizer 104 is stabilized, the output voltage $V_{AMP}$ can be a smoothed signal that converges in a narrow range and is smoothed. In the example shown in FIG. 14, after the exchange of the capsule 106 is promoted in step S1101, the elapse of a predetermined time is waited in step S1102. After that, the resistance value $R_{HTR}$ and the reference temperature $T_{ref}$ are detected and stored in the memory. The processing shown in FIG. 14 is processing (first processing) of acquiring the reference resistance value $R_{ref}$ after waiting for the elapse of a predetermined time after the user is promoted to do the exchange via the user interface 116.

More specifically, in step S1103, the processor 240 turns off the switch SW1, and turns on the switch SW2. In step S1104, the processor 240 detects the output voltage $V_{AMP}$ of the amplifier AMP of the detection circuit 220, and calculates the resistance value $R_{HTR}$ of the heater 127 in accordance with equations (2) and (4) based on the detected output voltage $V_{AMP}$. In step S1105, the processor 240 turns on the switch SW1, and turns off the switch SW2.

In step S1106, the processor 240 stores the resistance value $R_{HTR}$ obtained by the calculation in step S1104 in the memory as the reference resistance value $R_{ref}$. In step S1107, the processor 240 acquires the temperature of a predetermined portion of the inhalation device 100, and stores the temperature in the memory as the reference temperature $T_{ref}$. In step S1108, the processor 240 cancels inhibition of feed control for the heater 127.

Figure 16:
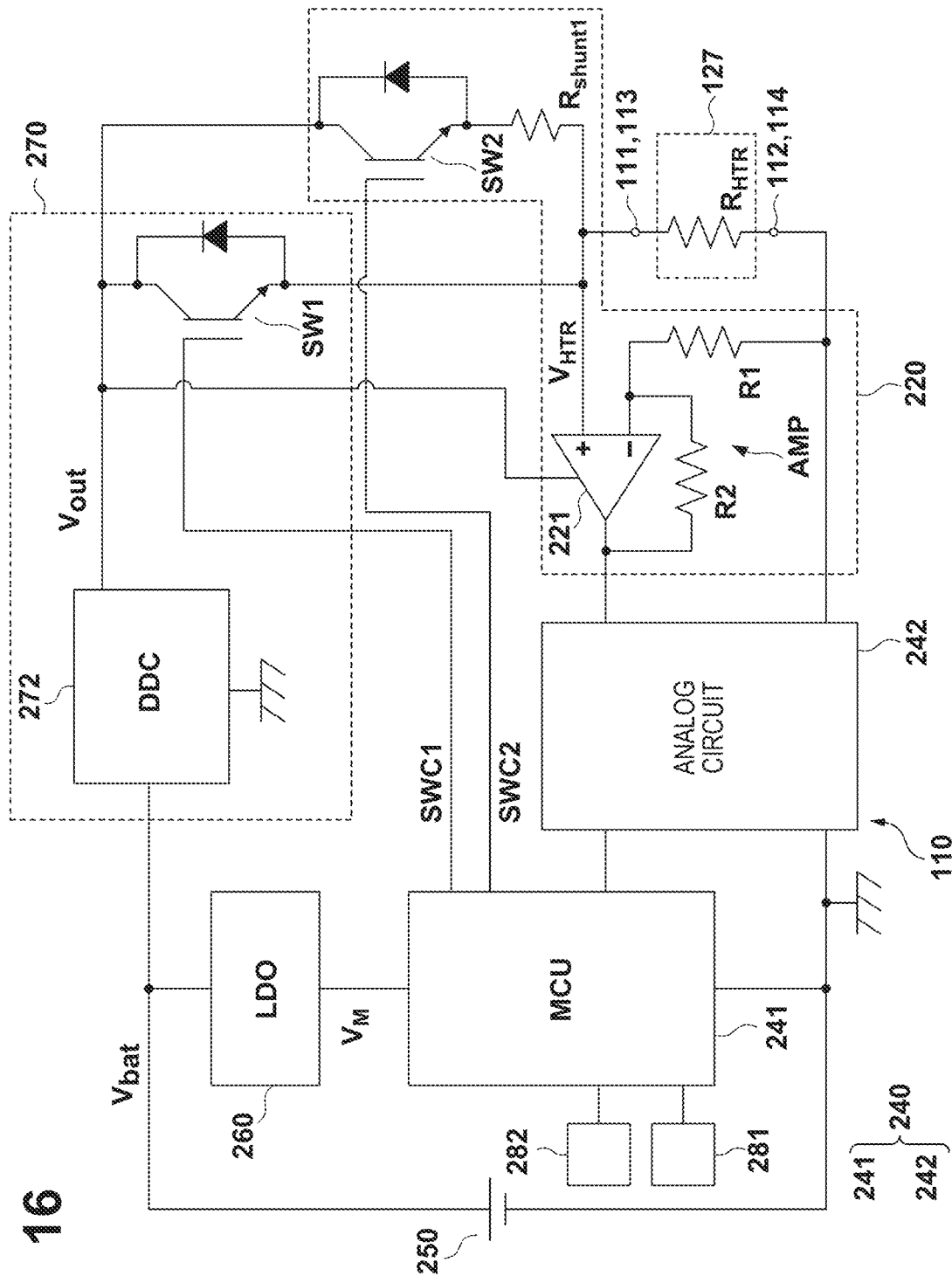
FIG. 16 is a view showing an example in which calculation of a smoothed signal is implemented by an analog circuit.
Figure 17:
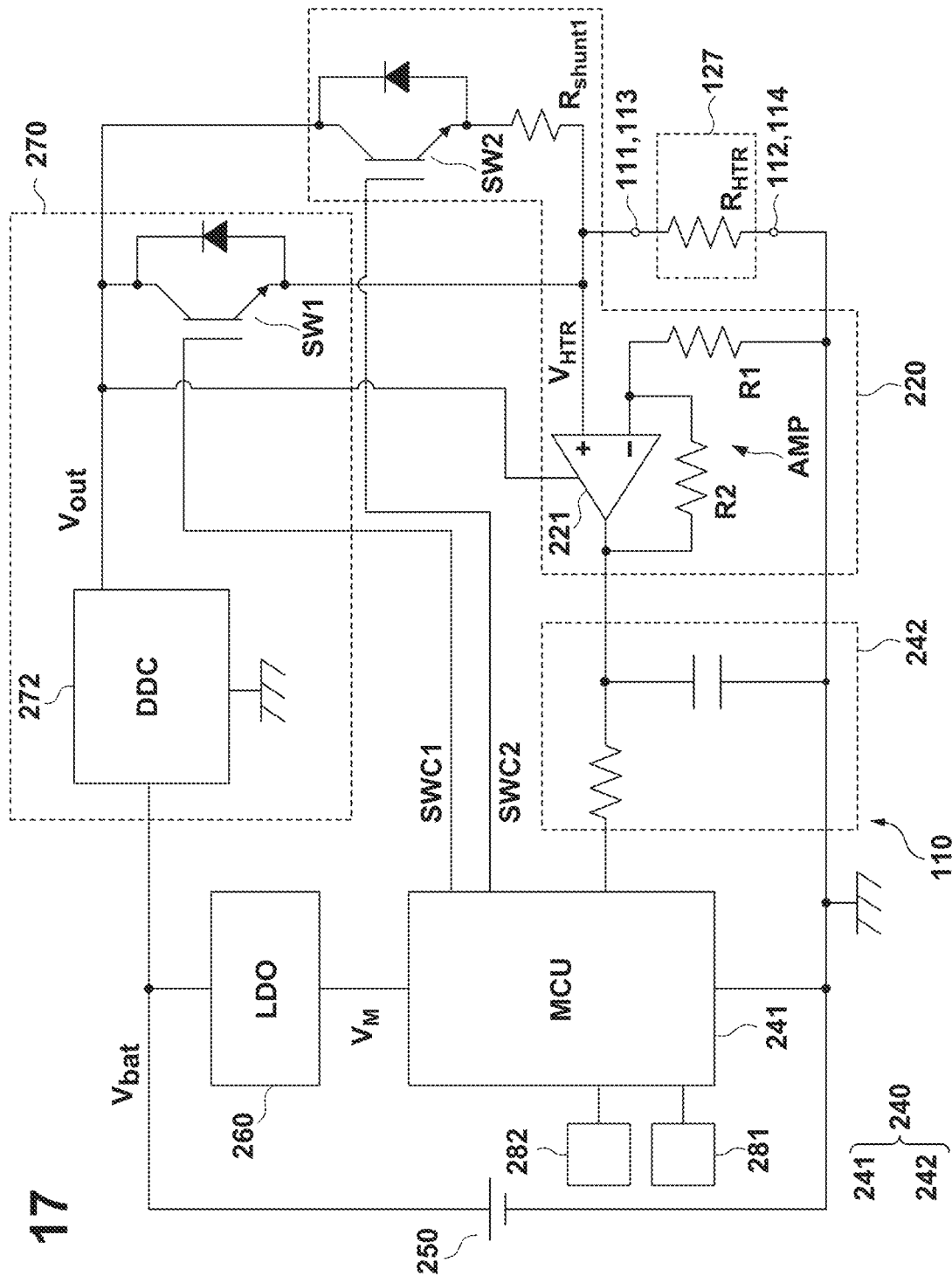
FIG. 17 is a view showing a detailed example in which calculation of a smoothed signal is implemented by an analog circuit.
Figure 18:
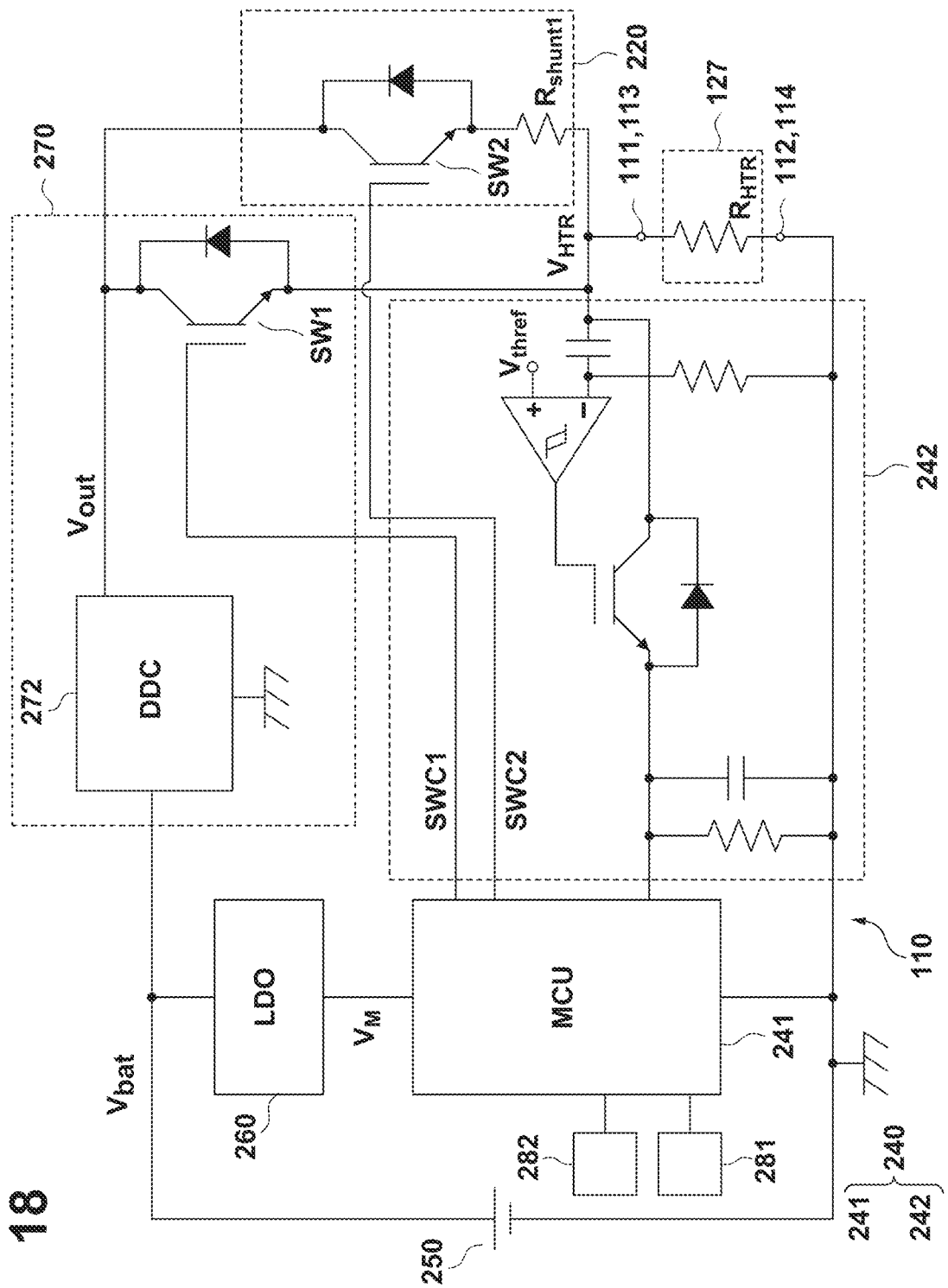
FIG. 18 is a view showing a detailed example in which calculation of a smoothed signal is implemented by an analog circuit.

As shown in FIG. 16, the processor 240 may include an analog circuit (smoothing circuit) 242 that generates the above-described smoothed signal, and an MCU 241 to which the output signal of the analog circuit 242 is input. The analog circuit 242 can generate the smoothed signal by, for example, a method according to one of the above-described first to fourth examples. The analog circuit 242 can include, for example, a circuit that generates an average value such as a moving average value, an LPF circuit that executes LPF processing, or a peak removing circuit that removes a peak. An averaging circuit that calculates an average value such as a moving average value is shown in, for example, FIG. 1 and the like of Japanese Patent Laid-Open No. 2000-278659. FIG. 17 shows the arrangement of the inhalation device 100 including the analog circuit 242 including an LPF circuit. FIG. 18 shows the arrangement of the inhalation device 100 including the analog circuit 242 including a peak removing circuit.

Figure 19:
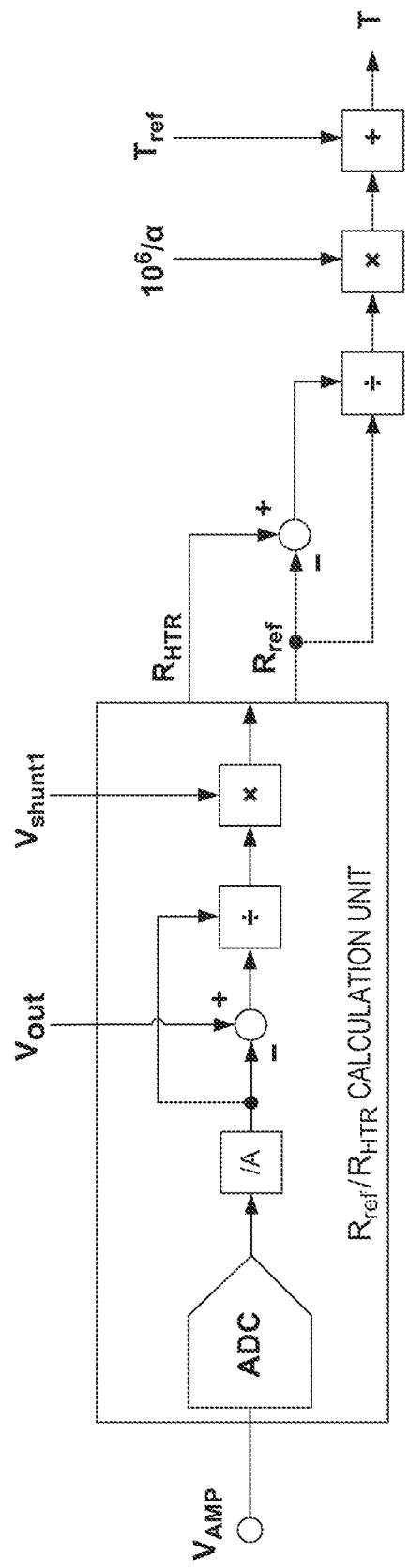
FIG. 19 is a view showing a detailed example in which calculation of a resistance value $R_{HTR}$ of a heater is implemented by an analog circuit.

Calculations exemplified as equations (2) and (4) may be implemented by an analog circuit. FIG. 19 shows an analog circuit that calculates the resistance value $R_{HTR}$ of the heater 127 in accordance with equations (2) and (4). This analog circuit may be incorporated in the MCU that constitutes the processor 240 or may be provided separately from the MCU.

Processing of detecting, by the processor 240 of the controller 102, exchange of the atomizer 104, that is, detachment of the atomizer 104 from (the holding portion 103 of) the controller 102, and attachment of the atomizer 104 to (the holding portion 103 of) the controller 102 will be described below. In the first arrangement example shown in FIG. 2, the output voltage $V_{AMP}$ of the amplifier AMP of the detection circuit 220 in a holding state in which the atomizer 104 is held by the holding portion 103 of the controller 102 is given by $$V_{AMP}=A\cdot V_{HTR}=A\cdot V_{out}R_{HTR}/(R_{shunt1}+R_{HTR}) \quad (6)$$

Here, the voltage $V_{HTR}$ according to the voltage of the node (for example, the electrical contact 111) on the current path that supplies a current to the heater 127 is input to (the noninverting input terminal of) the amplifier AMP. The voltage $V_{HTR}$ can be a voltage having correlation with the voltage of the node. In an example, the voltage $V_{HTR}$ can be a voltage equal to the voltage of the node. Alternatively, the voltage $V_{HTR}$ may be, for example, a voltage obtained by dividing the voltage of the electrical contact 111 or a voltage obtained by amplifying the voltage of the electrical contact 111. The output voltage $V_{AMP}$ is the output of the amplifier AMP, which is provided to the processor 240. The processor 240 can acquire information from the amplifier AMP and execute control according to the information. The information that the processor 240 acquires from the amplifier AMP may be the output voltage $V_{AMP}$, or may be information derived from the output voltage $V_{AMP}$.

Figure 20:
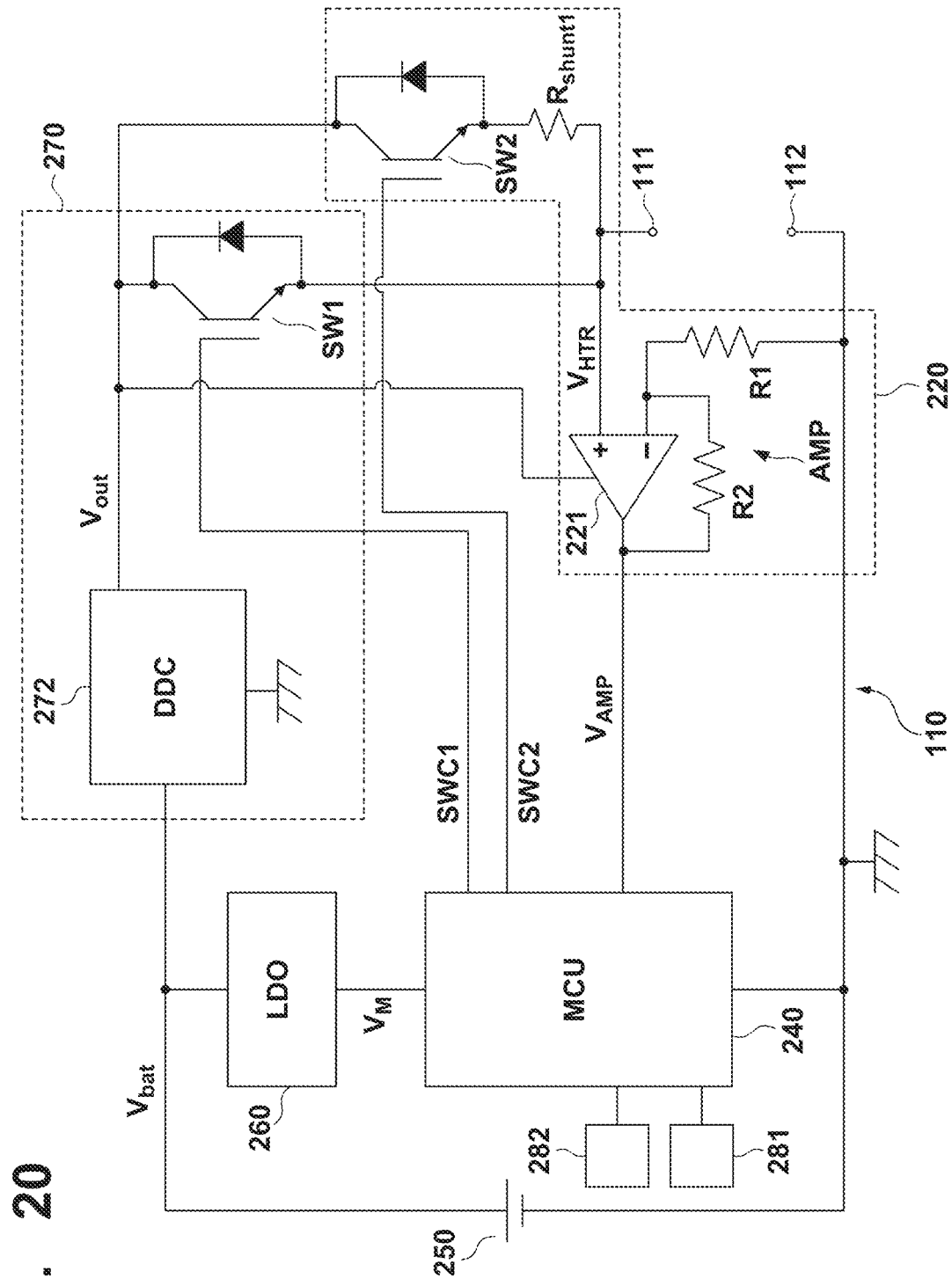
FIG. 20 is a view showing a state in which the heater of an atomizer is not attached to the electric component of the first arrangement example shown in FIG. 2.

FIG. 20 shows a non-holding state in which the atomizer 104 is not held by the holding portion 103 of the controller 102 in the first arrangement example. In the non-holding state, the heater 127 does not exist between the first electrical contact 111 and the second electrical contact 112. In the first arrangement example, since the heater driving voltage \Tout appears at the first electrical contact 111, the output voltage $V_{AMP}$ of the amplifier AMP of the detection circuit 220 in the non-holding state is given by $$V_{AMP}=A\cdot V_{HTR}=A\cdot V_{out} \quad (7)$$

Here, the amplification factor A and the shunt resistance value $R_{shunt1}$ can be decided such that a value that the output voltage $V_{AMP}$ of the amplifier AMP in the holding state can take satisfies the first range ($0<V_{AMP}<V_{TH}$), and a value that the output voltage $V_{AMP}$ of the amplifier AMP in the non-holding state can take satisfies the second range ($V_{TH}\leq V_{AMP}\leq V_{out}$). The second range can be set to the variation range of the power supply voltage \Tout supplied to the amplifier AMP. The first range and the second range can be set not to include ranges overlapping each other. The lower limit and the upper limit of the first range may be smaller than the lower limit and the upper limit of the second range, and a difference may be provided between the upper limit of the first range and the lower limit of the second range. Alternatively, the lower limit and the upper limit of the first range may be larger than the lower limit and the upper limit of the second range, and a difference may be provided between the lower limit of the first range and the upper limit of the second range.

Hence, the processor 240 can discriminately identify the holding state and the non-holding state based on the information acquired from the amplifier AMP. In addition, the processor 240 can detect transition from the holding state to the non-holding state and transition from the non-holding state to the holding state based on the information acquired from the amplifier AMP. Detection of transition from the holding state to the non-holding state means detection of detachment of the atomizer 104 from (the holding portion 103 of) the controller 102, and detection of transition from the non-holding state to the holding state means detection of attachment of the atomizer 104 to (the holding portion 103 of) the controller 102. In addition, the processor 240 can calculate the temperature of the heater 127 based on the information acquired from the amplifier AMP. Such an arrangement is advantageous in reducing the cost of the inhalation device 100 or the controller 102.

In the second arrangement example shown in FIG. 3, the output voltage $V_{AMP}$ of the amplifier AMP of the detection circuit 220 in the holding state in which the atomizer 104 is held by the holding portion 103 of the controller 102 is given by equation (8) (the same as equation (6)). However, the shunt resistance value $R_{shunt2}$ is sufficiently larger than the resistance value $R_{HTR}$ of the heater 127, as described above.

$$V_{AMP}=A\cdot V_{HTR}=A\cdot V_{out}R_{HTR}/(R_{shunt1}+R_{HTR}) \quad (8)$$

Figure 21:
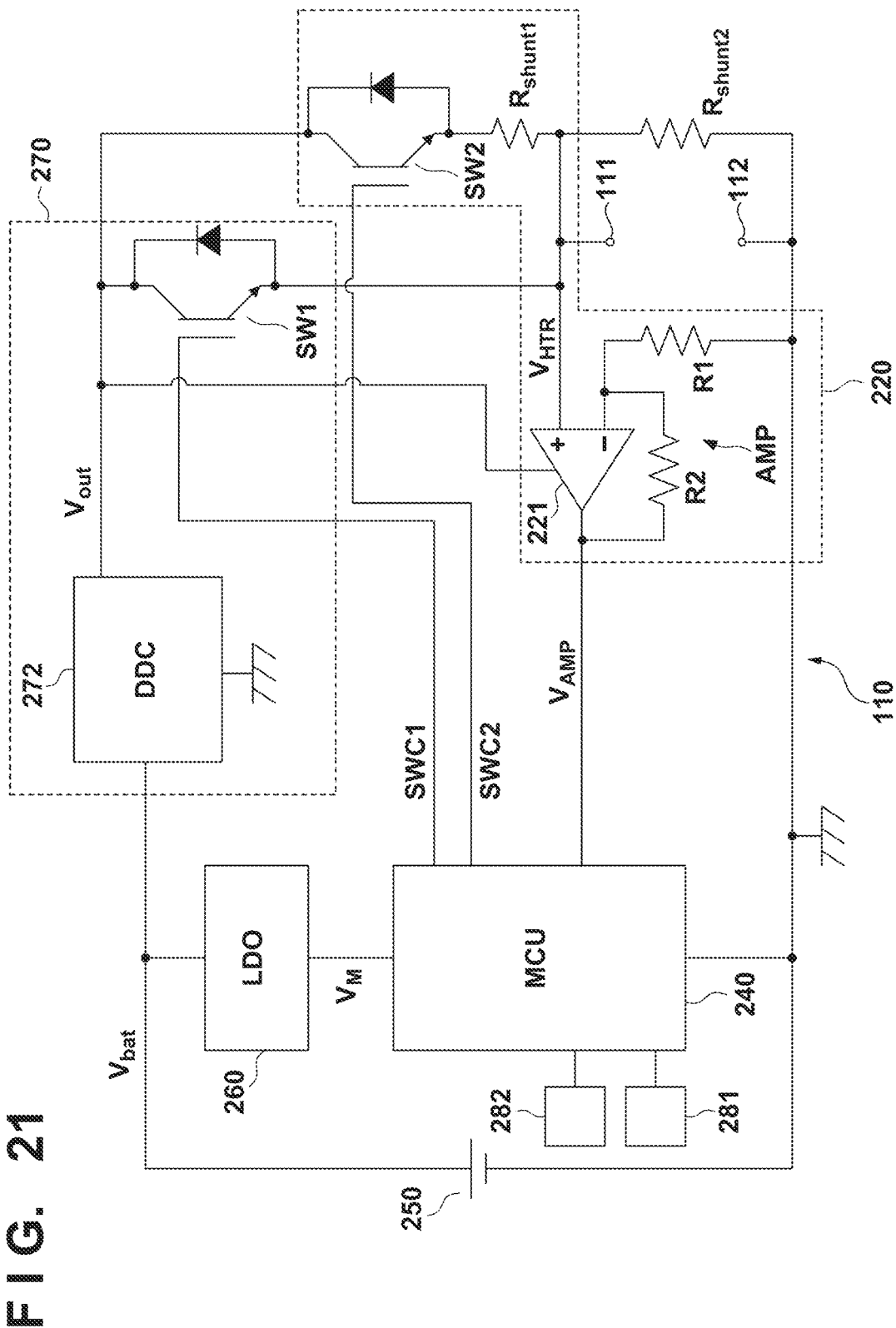
FIG. 21 is a view showing a state in which the heater of an atomizer is not attached to the electric component of the second arrangement example shown in FIG. 3.

FIG. 21 shows a non-holding state in which the atomizer 104 is not held by the holding portion 103 of the controller 102 in the second arrangement example. In the non-holding state, the heater 127 does not exist between the first electrical contact 111 and the second electrical contact 112. In the second arrangement example, the output voltage $V_{AMP}$ of the amplifier AMP of the detection circuit 220 in the non-holding state is given by $$V_{AMP}=A\cdot V_{HTR}=A\cdot V_{out}R_{shunt2}/(R_{shunt1}+R_{shunt2}) \quad (9)$$

Here, the amplification factor A and the shunt resistance values $R_{shunt1}$ and $R_{shunt2}$ can be decided such that a value that the output voltage $V_{AMP}$ of the amplifier AMP in the holding state can take satisfies the first range ($0<V_{AMP}<V_{TH}$), and a value that the output voltage $V_{AMP}$ of the amplifier AMP in the non-holding state can take satisfies the second range ($V_{TH}\leq V_{AMP}\leq V_{out}$). The first range and the second range can be set not to include ranges overlapping each other. The lower limit and the upper limit of the first range may be smaller than the lower limit and the upper limit of the second range, and a difference may be provided between the upper limit of the first range and the lower limit of the second range. Alternatively, the lower limit and the upper limit of the first range may be larger than the lower limit and the upper limit of the second range, and a difference may be provided between the lower limit of the first range and the upper limit of the second range.

Hence, the processor 240 can discriminately identify the holding state and the non-holding state based on the information acquired from the amplifier AMP. In addition, the processor 240 can detect transition from the holding state to the non-holding state and transition from the non-holding state to the holding state based on the information acquired from the amplifier AMP. Also, the processor 240 can calculate the temperature of the heater 127 based on the information acquired from the amplifier AMP. Such an arrangement is advantageous in reducing the cost of the inhalation device 100 or the controller 102.

In the third arrangement example shown in FIG. 4, the output voltage $V_{AMP}$ of the amplifier AMP of the detection circuit 220 in the holding state in which the atomizer 104 is held by the holding portion 103 of the controller 102 is given by equation (10) (the same as equations (6) and (8)).

$$V_{AMP}=A\cdot V_{HTR}=A\cdot V_{out}R_{HTR}/(R_{shunt1}+R_{HTR}) \quad (10)$$

Figure 22:
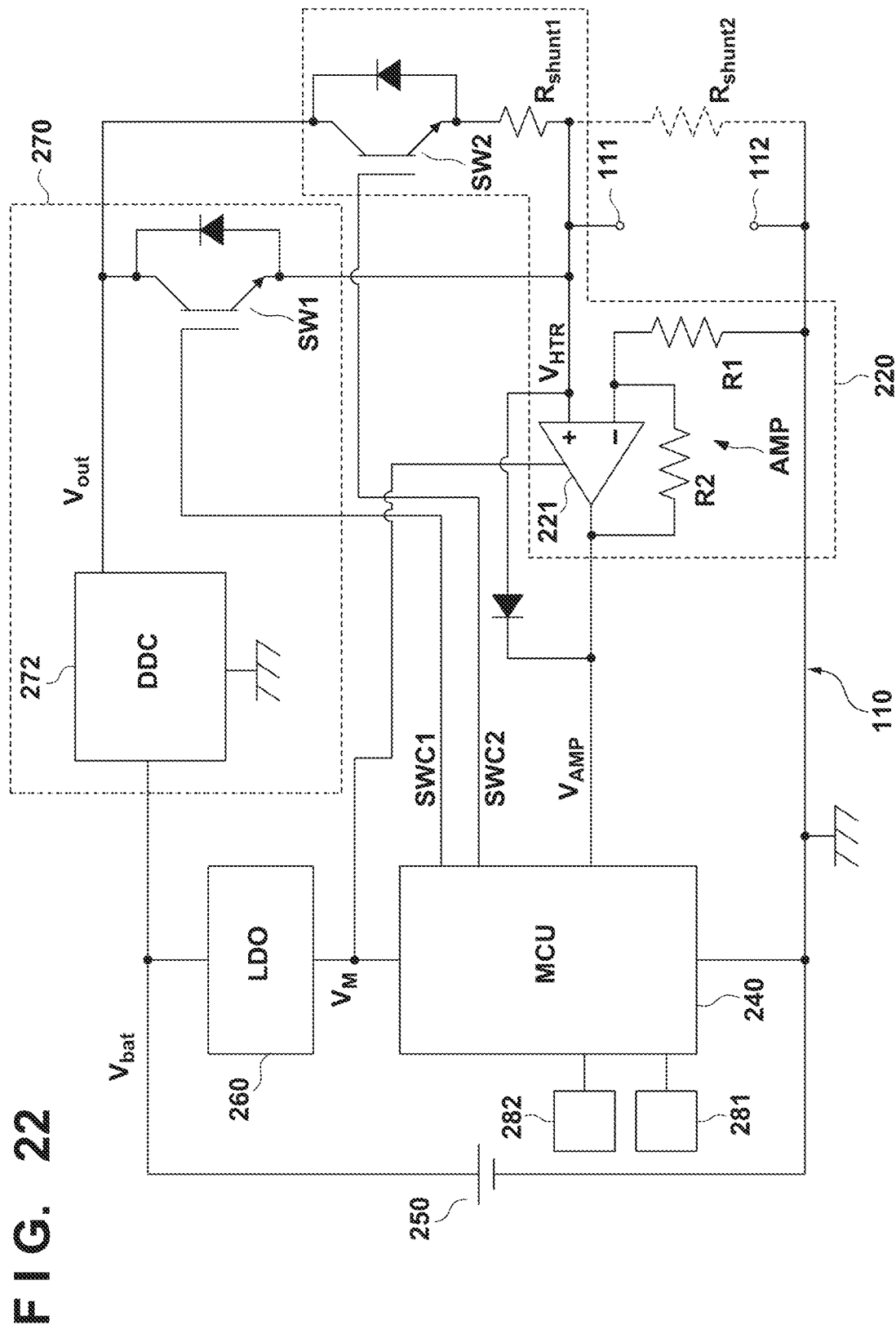
FIG. 22 is a view showing a state in which the heater of an atomizer is not attached to the electric component of the third arrangement example shown in FIG. 4.

FIG. 22 shows a non-holding state in which the atomizer 104 is not held by the holding portion 103 of the controller 102 in the third arrangement example. In the non-holding state, the heater 127 does not exist between the first electrical contact 111 and the second electrical contact 112. In the third arrangement example, if the shunt resistor $R_{shunt2}$ does not exist, and $V_M<V_{out}$, the output voltage $V_{AMP}$ of the amplifier AMP of the detection circuit 220 in the non-holding state is given by $$V_{AMP}=V_M \quad (11)$$

This can be understood from the fact that the maximum value of the output voltage $V_{AMP}$ of the amplifier AMP is $V_M$. Additionally, in the third arrangement example, as for the output voltage $V_{AMP}$ of the amplifier AMP of the detection circuit 220 in the non-holding state, in a case in which the shunt resistor $R_{shunt2}$ exists, and $V_M < V_{out}$, if equation (12) is satisfied, the output voltage $V_{AMP}$ becomes equal to the voltage $V_M$, as indicated by equation (11). In this case, the output voltage $V_{AMP}$ of the amplifier AMP in the non-holding state has the maximum value of the voltage that the amplifier AMP can output. Hence, the first range that the value of the output voltage $V_{AMP}$ of the amplifier AMP in the holding state can take can be made large, that is, the resolution can be made high without overlapping the first range that the value of the output voltage $V_{AMP}$ of the amplifier AMP in the non-holding state can take.

$$(R_{shunt2}/(R_{shunt1}+R_{shunt2})) \cdot V_{out} > V_M \qquad (12)$$

On the other hand, in the third arrangement example, in a case in which the shunt resistor $R_{shunt2}$ exists, and $V_M > V_{out}$, the output voltage $V_{AMP}$ of the amplifier AMP of the detection circuit 220 in the non-holding state is given by $$V_{AMP} = A \cdot V_{HTR} = A \cdot V_{out} \cdot R_{shunt2}/(R_{shunt1}+R_{shunt2}) \qquad (13)$$

Here, the amplification factor A and the shunt resistance values $R_{shunt1}$ and $R_{shunt2}$ can be decided such that a value that the output voltage $V_{AMP}$ of the amplifier AMP in the holding state can take satisfies the first range ($0 < V_{AMP} < V_{TH}$), and a value that the output voltage $V_{AMP}$ of the amplifier AMP in the non-holding state can take satisfies the second range ($V_{TH} \leq V_{AMP} \leq V_M$). The first range and the second range do not include ranges overlapping each other. The lower limit and the upper limit of the first range may be smaller than the lower limit and the upper limit of the second range, and a difference may be provided between the upper limit of the first range and the lower limit of the second range. Alternatively, the lower limit and the upper limit of the first range may be larger than the lower limit and the upper limit of the second range, and a difference may be provided between the lower limit of the first range and the upper limit of the second range.

Hence, the processor 240 can discriminately identify the holding state and the non-holding state based on the information acquired from the amplifier AMP. In addition, the processor 240 can detect transition from the holding state to the non-holding state and transition from the non-holding state to the holding state based on the information acquired from the amplifier AMP. Also, the processor 240 can calculate the temperature of the heater 127 based on the information acquired from the amplifier AMP. Such an arrangement is advantageous in reducing the cost of the inhalation device 100 or the controller 102.

The above-described output voltage $V_{AMP}$ of the amplifier AMP is an example of the information obtained from the amplifier AMP. The information obtained from the amplifier AMP may be, for example, another information that the processor 240 can derive from the output voltage $V_{AMP}$. Such another information can be, for example, the resistance value $R_{HTR}$ calculated from the output voltage $V_{AMP}$. The processor 240 can discriminately identify the holding state and the non-holding state based on the resistance value $R_{HTR}$. In addition, the processor 240 can detect transition from the holding state to the non-holding state and transition from the non-holding state to the holding state.

Let Rill be the resistance value $R_{HTR}$ of the heater 127 when the output voltage $V_{AMP}$ of the amplifier AMP is $V_{TH}$. If the calculated resistance value $R_{HTR}$ is smaller than $R_{TH}$, the processor 240 can determine that the atomizer is in the holding state. On the other hand, if the calculated resistance value $R_{HTR}$ is equal to or larger than Rill, the processor 240 can determine that the atomizer is in the non-holding state.

FIG. 27 shows a change of a state concerning holding and non-holding of the atomizer 104 by the holding portion 103 of the controller 102. Referring to FIG. 27, "holding" represents the holding state in which the atomizer 104 is held by the holding portion 103 of the controller 102. "Non-holding" represents the non-holding state in which the atomizer 104 is not held by the holding portion 103 of the controller 102. "Detachment" represents a detaching work state in which the user is performing an operation of detaching the atomizer 104 from the holding portion 103 of the controller 102. "Attachment" represents an attaching work state in which the user is performing an operation of attaching the atomizer 104 to the holding portion 103 of the controller 102.

In FIG. 27, the abscissa represents the elapse of time, and the ordinate represents the resistance value Rum. The measurement upper limit is the above-described $R_{TH}$. That the resistance value $R_{HTR}$ is equal to or larger than the measurement upper limit ($R_{TH}$) formally represents that the resistance value $R_{HTR}$ belongs to the second range, that is, that the atomizer 104 is detached from the holding portion 103 of the controller 102, thereby setting the non-holding state in which the atomizer 104 is not held by the holding portion 103. On the other hand, that the resistance value $R_{HTR}$ is smaller than the measurement upper limit ($R_{TH}$) formally represents that the resistance value $R_{HTR}$ belongs to the first range, that is, the holding state in which the atomizer 104 is held by the holding portion 103 of the controller 102.

In the holding state, the resistance value $R_{HTR}$ can have a slight variation. In the non-holding state, the resistance value $R_{HTR}$ can have a predetermined value. In the detaching work state, the resistance value $R_{HTR}$ can largely vary and exhibit the same value as in the holding state or the same value as in the non-holding state. In the attaching work state, the resistance value $R_{HTR}$ can largely vary, and a long time may be needed until the resistance value $R_{HTR}$ obtains the value in the holding state. Thus, in step S619 of detection associated processing shown in FIGS. 6A and 6B, if the state of the holding portion 103 is determined simply based on the instantaneous magnitude of the resistance value $R_{HTR}$, completion of the exchange work of the atomizer 104 may erroneously be determined.

Figure 23A:
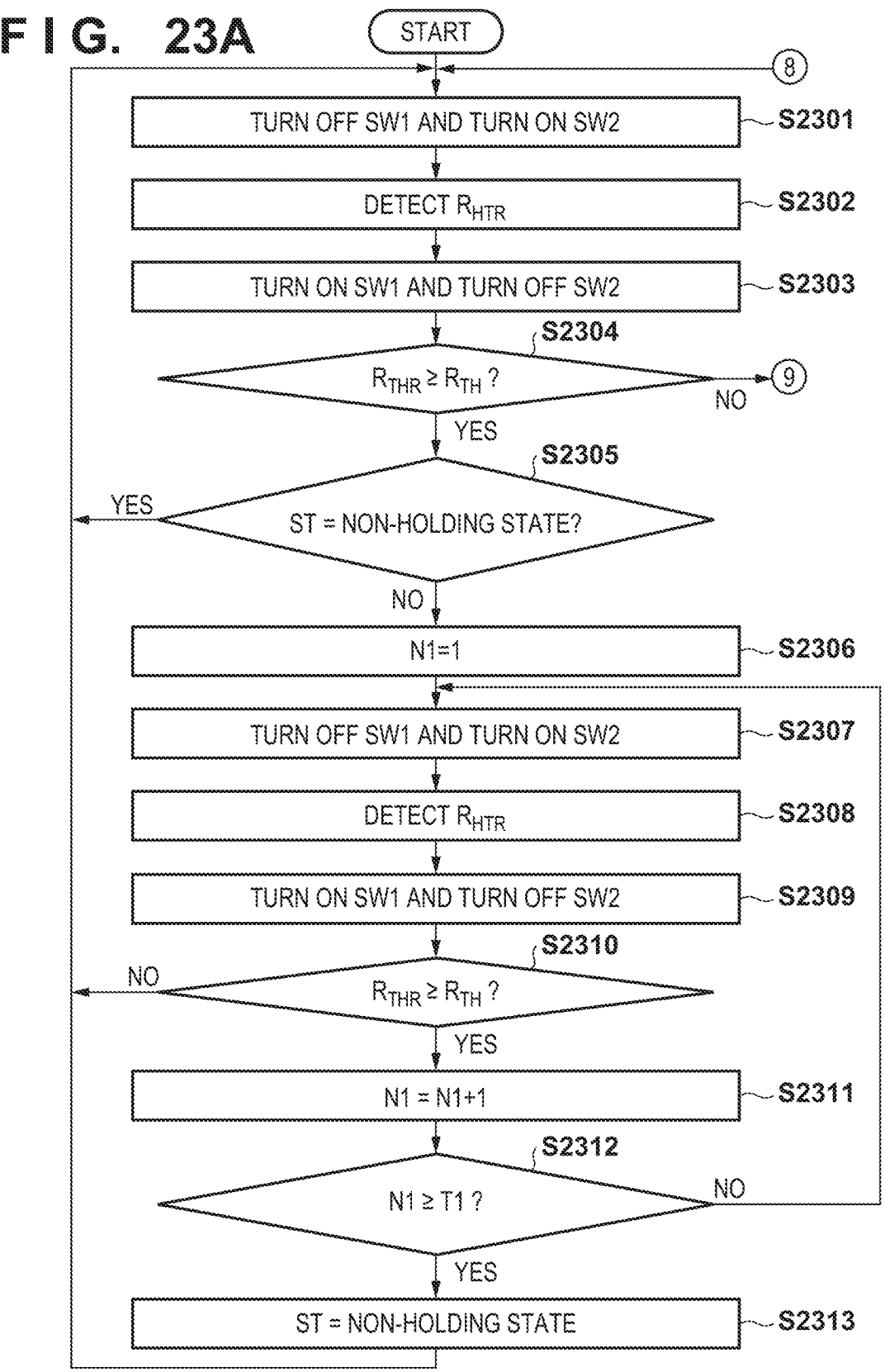
FIGS. 23A and 23B show a flowchart showing monitoring processing of monitoring, by a processor, information obtained from the amplifier of a detection circuit.
Figure 23B:
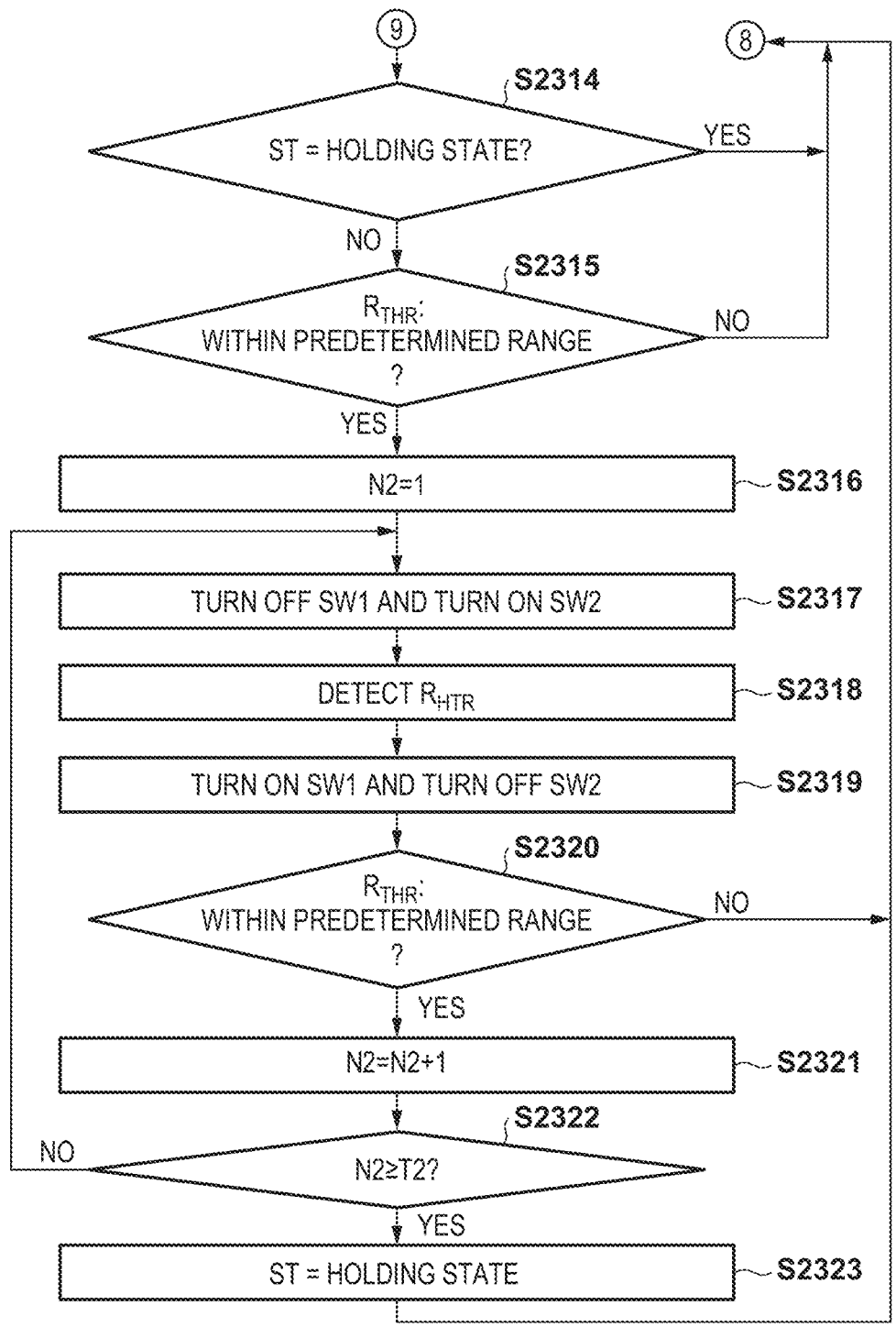

Control advantageous in preventing or reducing determination errors concerning completion of the exchange work of the atomizer 104 will be described below. FIGS. 23A and 23B show monitoring processing of monitoring information obtained from the amplifier AMP of the detection circuit 220. Monitoring processing is executed by the processor 240 separately from the processing shown in FIGS. 5 and 6. In step S619 of detection associated processing shown in FIGS. 6A and 6B, based on a change of the state of the holding portion 103 of the controller 102 managed by the monitoring processing shown in FIGS. 23A and 23B, the processor 240 can determine or detect that the exchange of the atomizer 104 has been done. In the processing shown in FIGS. 23A and 23B, as the information obtained from the amplifier AMP of the detection circuit 220, the resistance value $R_{HTR}$ of the heater 127 calculated based on the output voltage $V_{AMP}$ from the amplifier AMP is used. However, the information may be, for example, the output voltage $V_{AMP}$ itself or information having correlation with the output voltage $V_{AMP}$.

FIG. 26 shows transition of a control variable ST. Expressions in FIG. 26 are common to the expressions in FIGS. 25A and 25B. Processing shown in FIGS. 23A and 23B will be described below with reference to FIG. 26. In step S2301, the processor 240 turns off the switch SW1, and turns on the switch SW2. In step S2302, the processor 240 detects the output voltage $V_{AMP}$ of the amplifier AMP of the detection circuit 220, and calculates the resistance value $R_{HTR}$ of the heater 127 in accordance with equations (2) and (4) based on the detected output voltage $V_{AMP}$. In step S2303, the processor 240 turns on the switch SW1, and turns off the switch SW2.

In step S2304, the processor 240 determines whether the resistance value $R_{HTR}$ detected in step S2302 is equal to or larger than $R_{TH}$ (corresponding to the measurement upper limit shown in FIG. 27). If the resistance value $R_{HTR}$ is equal to or larger than $R_{TH}$, the processor 240 advances to step S2305. If the resistance value Rum is smaller than $R_{TH}$, the processor 240 advances to step S2314. Here, that the resistance value $R_{HTR}$ is equal to or larger than $R_{TH}$ formally represents that the resistance value $R_{HTR}$ belongs to the second range, that is, that the atomizer 104 is detached from the holding portion 103 of the controller 102, thereby setting the non-holding state in which the atomizer 104 is not held by the holding portion 103. On the other hand, that the resistance value Rum is smaller than Rill formally represents that the resistance value $R_{HTR}$ belongs to the first range, that is, the holding state in which the atomizer 104 is held by the holding portion 103 of the controller 102.

In step S2305, the processor 240 determines whether the control variable ST that is a variable for control indicates "non-holding state" or "holding state". That the control variable ST indicates "non-holding state" means that the processor 240 recognizes that the current state is the non-holding state in which the atomizer 104 is not held by the holding portion 103 of the controller 102. On the other hand, that the control variable ST indicates "holding state" means that the processor 240 recognizes that the current state is the holding state in which the atomizer 104 is held by the holding portion 103 of the controller 102. If the control variable ST indicates "non-holding state" in step S2305, the processor 240 returns to step S2301. If the control variable ST indicates "holding state", the processor 240 advances to step S2306. In the processing shown in FIGS. 23A and 23B, unless it is determined in step S2304 that the resistance value Rum is equal to or larger than $R_{TH}$, the determination in step S2305 is not executed. For this reason, even if the resistance value $R_{HTR}$ varies within the first range in the holding state (for example, P1 in FIG. 26) in which the atomizer 104 is held by the holding portion 103, the recognition of the holding state is continued.

In steps S2306 to S2313, if the resistance value $R_{HTR}$ that was in the first range ($<R_{TH}$) continuously falls within the second range ($\geq R_{TH}$), the processor 240 determines that transition from the holding state (for example, P1 in FIG. 26) to the non-holding state (for example, P3 in FIG. 26) is completed. More specifically, in step S2306, the processor 240 sets a variable N1 for control to 1. In step S2307, the processor 240 turns off the switch SW1, and turns on the switch SW2. In step S2308, the processor 240 detects the output voltage $V_{AMP}$ of the amplifier AMP of the detection circuit 220, and calculates the resistance value $R_{HTR}$ of the heater 127 in accordance with equations (2) and (4) based on the detected output voltage $V_{AMP}$. In step S2309, the processor 240 turns on the switch SW1, and turns off the switch SW2.

In step S2310, the processor 240 determines whether the resistance value $R_{HTR}$ detected in step S2308 is equal to or larger than $R_{TH}$. If the resistance value $R_{HTR}$ is equal to or larger than Rix, the processor 240 adds 1 to N1 in step S2311 and then advances to step S2312. If the resistance value $R_{HTR}$ is smaller than $R_{TH}$, the processor 240 returns to step S2301. In step S2312, the processor determines whether N1 has reached preset T1. If N1 has reached T1, the process advances to step S2313. Otherwise, the process returns to step S2307. T1 can be set such that the loop of steps S2307 to S2312 (for example, P2 in FIG. 26) continues for an arbitrary time within the range of, for example, 1.5 sec to 2.5 sec. In step S2313, the processor 240 sets or changes the control variable ST to "non-holding state".

In steps S2314 to S2323, if the resistance value Rim that was in the second range ($R_{TH}$) continuously falls within the first range ($<R_{TH}$), the processor 240 determines that transition from the non-holding state (for example, P3 in FIG. 26) to the holding state (for example, P5 in FIG. 26) is completed. More specifically, in step S2314, the processor 240 determines whether the control variable ST indicates "holding state" or "non-holding state". If the control variable ST indicates "holding state", the process returns to step S2301. If the control variable ST indicates "non-holding state", the process advances to step S2315.

In step S2315, the processor 240 determines whether the resistance value $R_{HTR}$ falls within a predetermined range of the first range Rill). If the resistance value $R_{HTR}$ falls within the predetermined range, the process advances to step S2316. Otherwise, the process returns to step S2301. Here, the predetermined range can be decided to guarantee that the resistance value Rim is the resistance value $R_{HTR}$ in the holding state. In step S2316, the processor 240 sets a variable N2 for control to 1. In step S2317, the processor 240 turns off the switch SW1, and turns on the switch SW2. In step S2318, the processor 240 detects the output voltage $V_{AMP}$ of the amplifier AMP of the detection circuit 220, and calculates the resistance value $R_{HTR}$ of the heater 127 in accordance with equations (2) and (4) based on the detected output voltage $V_{AMP}$. In step S2319, the processor 240 turns on the switch SW1, and turns off the switch SW2.

In step S2320, the processor 240 determines whether the resistance value $R_{HTR}$ detected in step S2318 falls within a predetermined range. If the resistance value $R_{HTR}$ falls within the predetermined range, the process advances to step S2321. Otherwise, the process returns to step S2301. Here, the predetermined range can be the same range as the predetermined range in step S2315, but may be a different range (for example, a smaller range). In step S2321, the processor 240 determines whether N2 has reached preset T2. If N2 has reached T2, the process advances to step S2323. Otherwise, the process returns to step S2317. T2 can be set such that the loop of steps S2317 to S2322 (for example, P4 in FIG. 26) continues for an arbitrary time within the range of, for example, 1.5 sec to 2.5 sec. In step S2323, the processor 240 sets or changes the control variable ST to "holding state".

The relationship between the first range and feed control started in step S504 of the processing shown in FIGS. 5A and 5B will be described here as an example. Feed control is executed in the holding state. In feed control, if the value of the output voltage $V_{AMP}$ of the amplifier AMP (the information obtained from the amplifier AMP) belongs to the third range in the first range, the processor 240 can control the power supply unit 270 (switch SW1) not to supply power to the heater 127. Additionally, in feed control, in a state in which the atomization request exists, if the value of the output voltage $V_{AMP}$ of the amplifier AMP (the information obtained from the amplifier AMP) belongs to the fourth range in the first range, the processor 240 can control the power supply unit 270 (switch SW1) based on the output voltage $V_{AMP}$. The third range and the fourth range can be set not to include ranges overlapping each other. The third range can be the target temperature range, and the fourth range can be a temperature range outside the target temperature range.

The relationship between the first range and feed control in the processing shown in FIGS. 6A and 6B will be described as another example. In the processing shown in FIGS. 6A and 6B, if the temperature Tim of the heater 127 exceeds 250° C., in step S628, the processor 240 inhibits heating of the heater 127 (feeding to the heater 127) for a predetermined period (for example, 11 sec). In this example, the temperature range of 250° C. or more is the third range in the first range, and a temperature range lower than 250° C. is the fourth range in the first range.

Figure 24A:
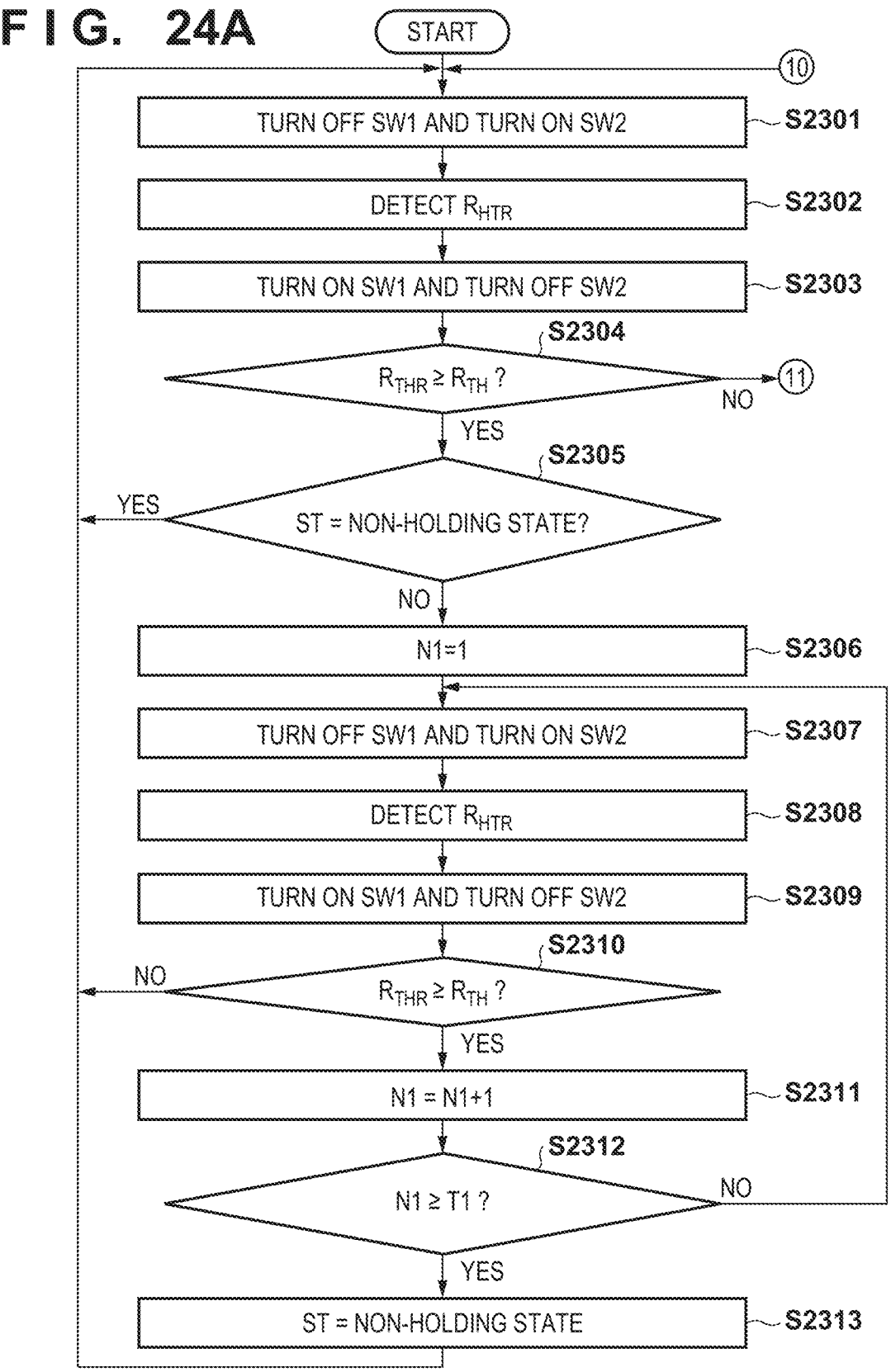
FIGS. 24A and 24B show a flowchart showing a modification of monitoring processing of monitoring, by the processor, information obtained from the amplifier of the detection circuit.
Figure 24B:
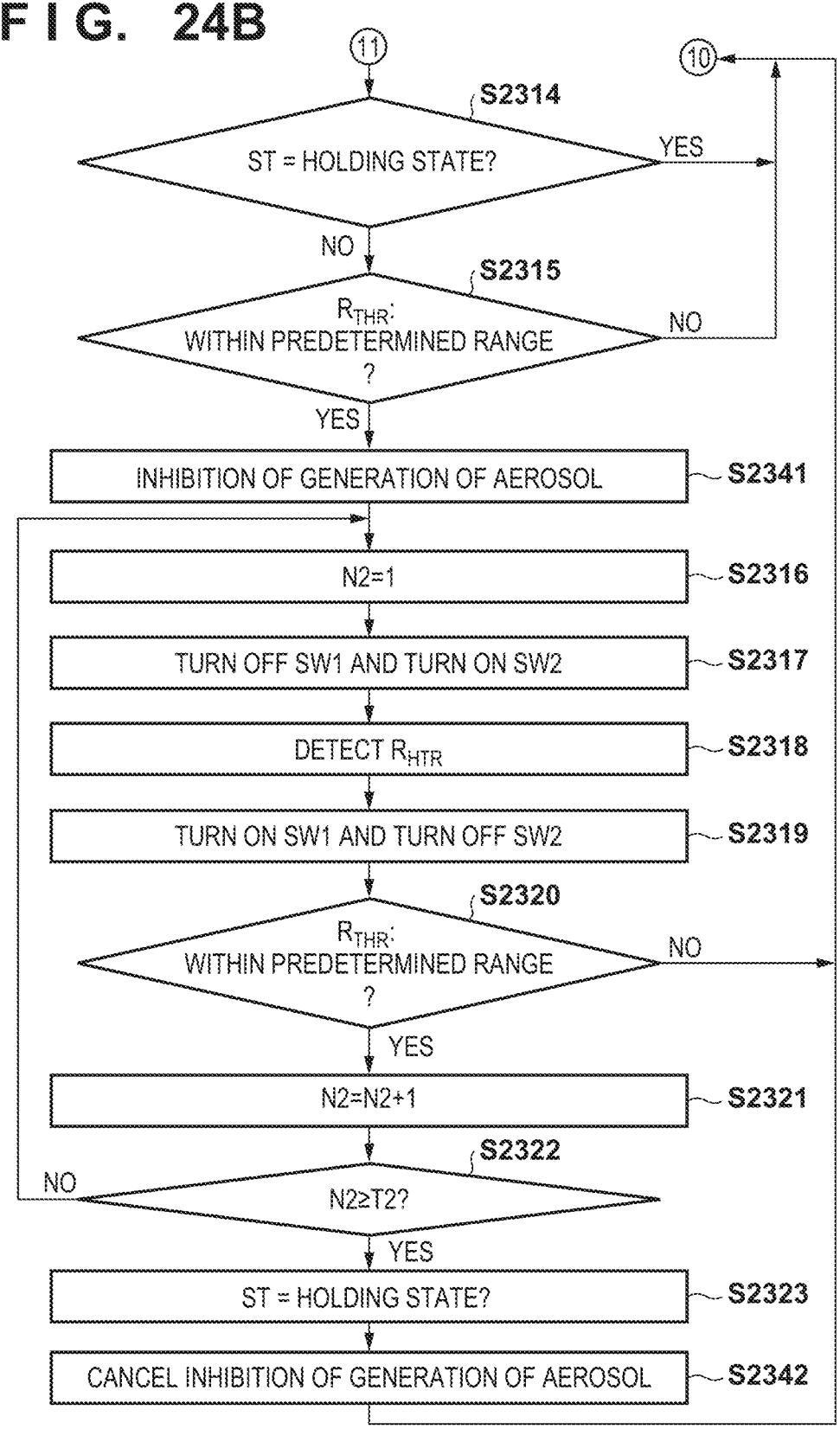

FIGS. 24A and 24B shows a modification of monitoring processing shown in FIGS. 23A and 23B. In monitoring processing shown in FIGS. 24A and 24B, steps S2341 and S2342 are added to the monitoring processing shown in FIGS. 23A and 23B. If it is determined in step S2315 that the resistance value Rum falls within a predetermined range of the first range $R_{TH}$), step S2341 is executed. In step S2341, the processor 240 inhibits generation of an aerosol, that is, heating of the heater 127 (feeding to the heater 127). Hence, generation of an aerosol is inhibited during the period indicated by P4 in FIG. 26.

After the control variable ST is set or changed to "holding state" in step S2323, step S2342 is executed. In step S2342, the processor 240 cancels inhibition of generation of an aerosol. Since this permits generation of an aerosol (feeding to the heater 127) only in the holding state in which the atomizer 104 is held by the holding portion 103 of the controller 102, the safety of the inhalation device 100 can be improved.

Figure 25A:
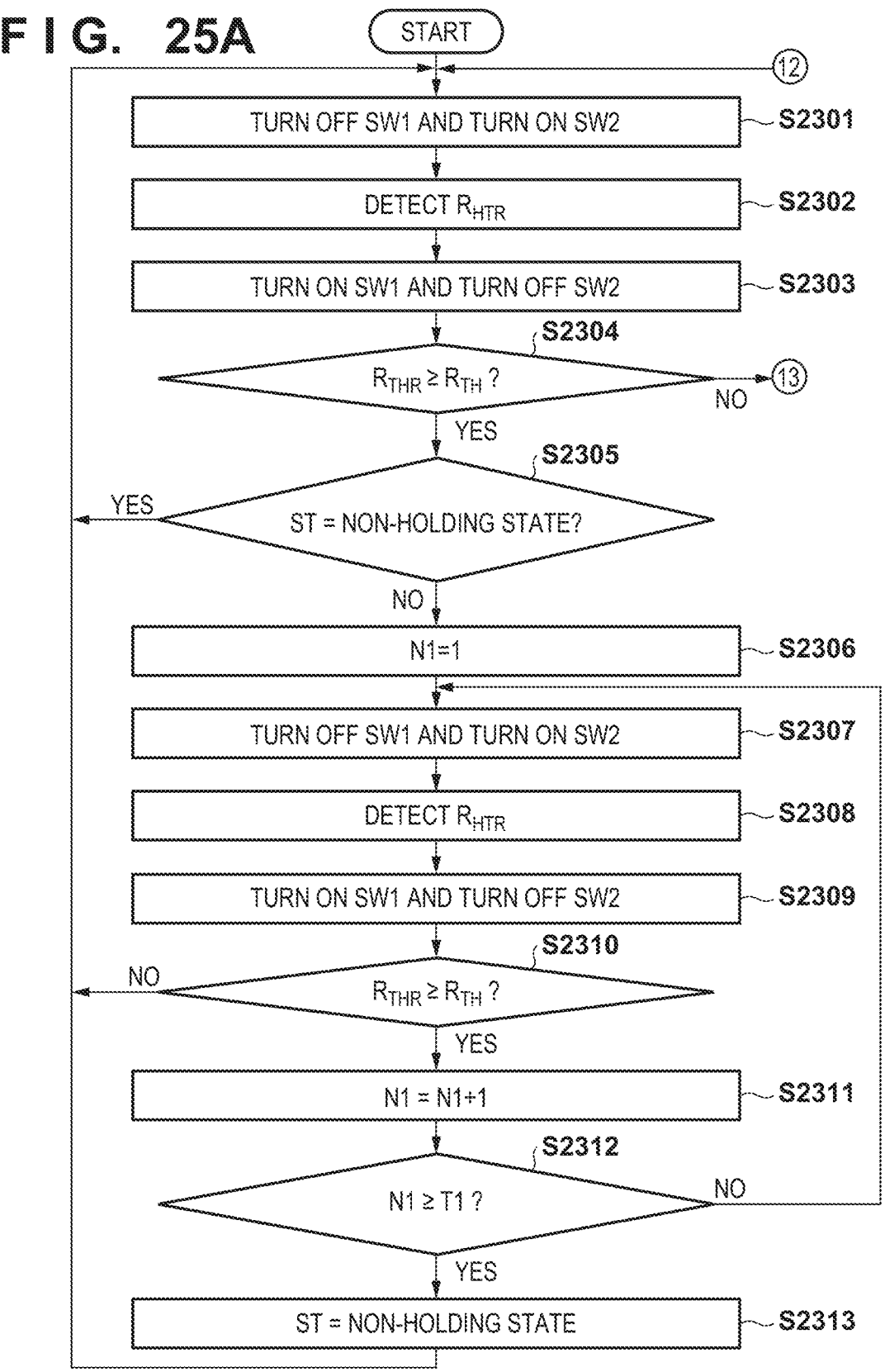
FIGS. 25A and 25B show a flowchart showing another modification of monitoring processing of monitoring, by the processor, information obtained from the amplifier of the detection circuit.
Figure 25B:
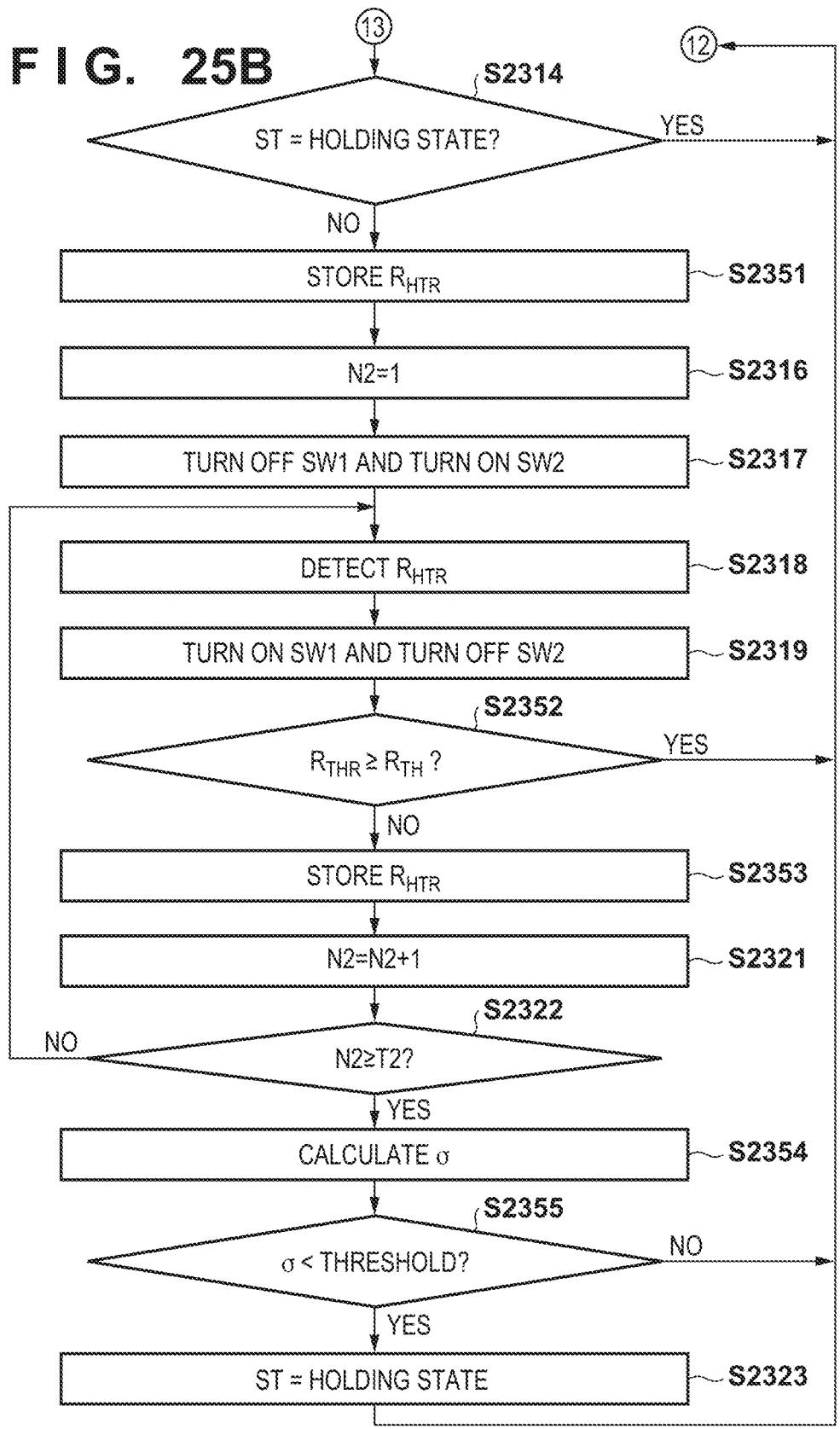

FIGS. 25A and 25B show another modification of monitoring processing shown in FIGS. 23A and 23B. In monitoring processing shown in FIGS. 25A and 25B, processing from step S2314 is different from the monitoring processing shown in FIGS. 23A and 23B. Processing from step S2314 will be described below.

In steps S2314 to S2323, if the resistance value $R_{HTR}$ that was in the second range ($\geq R_{TH}$) continuously falls within the first range ($<R_{TH}$), the processor 240 determines that transition from the non-holding state (for example, P3 in FIG. 26) to the holding state (for example, P5 in FIG. 26) is completed. More specifically, in step S2314, the processor 240 determines whether the control variable ST indicates "holding state" or "non-holding state". If the control variable ST indicates "holding state", the process returns to step S2301. If the control variable ST indicates "non-holding state", the process advances to step S2351.

In step S2351, the processor 240 stores the resistance value $R_{HTR}$ detected in step S2302 in the working area of the memory. In step S2316, the processor 240 sets the variable N2 for control to 1. In step S2317, the processor 240 turns off the switch SW1, and turns on the switch SW2. In step S2318, the processor 240 detects the output voltage $V_{AMP}$ of the amplifier AMP of the detection circuit 220, and calculates the resistance value $R_{HTR}$ of the heater 127 in accordance with equations (2) and (4) based on the detected output voltage $V_{AMP}$. In step S2319, the processor 240 turns on the switch SW1, and turns off the switch SW2.

In step S2352, the processor 240 determines whether the resistance value $R_{HTR}$ detected in step S2318 is equal to or larger than $R_{TH}$. If the resistance value $R_{HTR}$ is equal to or larger than $R_{TH}$, the processor 240 returns to step S2301. If the resistance value $R_{HTR}$ is smaller than $R_{TH}$, the processor 240 advances to step S2353.

In step S2353, the processor 240 stores the resistance value $R_{HTR}$ detected in step S2318 in the working area of the memory. In step S2321, the processor 240 determines whether N2 has reached T2. If N2 has reached T2, the process advances to step S2354. Otherwise, the process returns to step S2318. T2 can be set such that the loop of steps S2318 to S2322 (for example, P4 in FIG. 26) continues for an arbitrary time within the range of, for example, 1.5 sec to 2.5 sec.

In step S2354, the processor 240 calculates a standard variation a as an index representing the variation in the plurality of resistance values $R_{HTR}$ stored in the working area of the memory. In step S2355, the processor 240 determines whether a calculated in step S2354 is smaller than a predetermined threshold, that is, whether the resistance value $R_{HTR}$ has converged. If a is smaller than the predetermined threshold, the processor 240 advances to step S2323. Otherwise, the processor 240 returns to step S2301. In step S2323, the processor 240 sets or changes the control variable ST to "holding state".

As shown in FIG. 26, the processor 240 recognizes or determines the detaching work state as the holding state, and recognizes or determines the attaching work state as the non-holding state. Hence, in step S619 of detection associated processing shown in FIGS. 6A and 6B, the processor 240 can correctly determine or detect that the exchange of the atomizer 104 has been done.

The invention is not limited to the foregoing embodiments, and various variations/changes are possible within the spirit of the invention.

What is claimed is:

1. An inhalation device comprising:
  a holding portion configured to hold an atomizer including a heater configured to heat an aerosol source;
  a power supply configured to supply power to the heater of the atomizer attached to the holding portion;
  an amplifier to which a voltage according to a voltage of a node on a current path configured to supply the power to the heater is input; and
  a processor configured to acquire information from the amplifier and execute control according to the information, wherein
  the information takes a voltage value in a first range in a holding state in which the holding portion holds the atomizer, and takes a voltage value in a second range in a non-holding state in which the holding portion does not hold the atomizer, and the first range and the second range do not include ranges overlapping each other,
  an upper limit of the first range is smaller than a power supply voltage supplied to a power supply terminal of the amplifier, and a lower limit of the second range is larger than the upper limit of the first range, and
  the processor determines, based on the voltage value of the information, whether a state of the holding portion is in the holding state or the non-holding state.

2. The inhalation device according to claim 1, wherein the processor executes processing of acquiring the resistance value of the heater as a reference resistance value based on the voltage value of the information in accordance with transition from the non-holding state to the holding state.

3. The inhalation device according to claim 2, wherein the processor calculates the temperature of the heater based on the value of the information and the reference resistance value.

4. The inhalation device according to claim 2, wherein if the value of the information that was in the second range continuously falls within the first range, the processor is determine that the transition from the non-holding state to the holding state is completed.

5. The inhalation device according to claim 4, wherein upon determining that the transition from the non-holding state to the holding state is completed, the processor acquires and stores the reference resistance value of the heater.

6. The inhalation device according to claim 5, wherein in the holding state and in a state in which a request for operating the atomizer exists, the processor controls the power supply based on the reference resistance value and the resistance value of the heater, which is obtained based on the information, such that the heater obtains a target temperature.

7. The inhalation device according to claim 2, wherein if the value of the information that was in the first range continuously falls within the second range, the processor determines that the transition from the holding state to the non-holding state is completed.

8. The inhalation device according to claim 1, wherein if the value of the information belongs to a third range in the first range in the holding state, the processor controls the power supply not to supply power to the heater.

9. The inhalation device according to claim 8, wherein in the holding state and in a state in which a request for operating the atomizer exists, if the value of the information belongs to a fourth range in the first range, the processor controls the power supply based on the information, and
wherein the third range and the fourth range do not include ranges overlapping each other.

10. The inhalation device according to claim 1, wherein the second range is a variation range of the power supply voltage.

11. The inhalation device according to claim 1, wherein in the non-holding state, a voltage equal to the power supply voltage supplied to the power supply terminal of the amplifier is input to the input terminal of the amplifier.

12. The inhalation device according to claim 1, wherein the holding portion includes a first electrical contact and a second electrical contact, the first electrical contact is electrically connected to the output terminal of the power supply via a first resistive element and contacts a third electrical contact provided in the atomizer, the second electrical contact is electrically connected to a ground line and contacts a fourth electrical contact provided in the atomizer, and
wherein the amplifier includes a noninverting input terminal electrically connected to the first electrical contact, and an inverting input terminal electrically connected to the second electrical contact.

13. The inhalation device according to claim 12, wherein the first electrical contact and the second electrical contact is electrically connected by a second resistive element.

14. The inhalation device according to claim 13, wherein letting $R_{shunt1}$ be the resistance value of the first resistive element, $R_{shunt2}$ be the resistance value of the second resistive element, $V_{out}$ be the voltage supplied to the first resistive element by the power supply, and $V_M$ be the power supply voltage supplied to the power supply terminal of the amplifier, $$(R_{shunt2}/(R_{shunt1}+R_{shunt2}))V_{out} > V_M$$

is satisfied in the non-holding state.

15. The inhalation device according to claim 12, wherein the inverting input terminal is grounded via a third resistive element, and the inverting input, terminal and the output terminal of the amplifier is connected via a fourth resistive element.

* * * * *